(12) United States Patent
Kasai et al.

(10) Patent No.: US 8,344,324 B2
(45) Date of Patent: Jan. 1, 2013

(54) INSPECTION APPARATUS AND INSPECTION METHOD USING ELECTROMAGNETIC WAVE

(75) Inventors: Shintaro Kasai, Yokohama (JP); Toshihiko Ouchi, Machida (JP); Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 310 days.

(21) Appl. No.: 12/682,248

(22) PCT Filed: Nov. 27, 2008

(86) PCT No.: PCT/JP2008/071993
§ 371 (c)(1),
(2), (4) Date: Apr. 8, 2010

(87) PCT Pub. No.: WO2009/069818
PCT Pub. Date: Jun. 4, 2009

(65) Prior Publication Data
US 2010/0252738 A1 Oct. 7, 2010

(30) Foreign Application Priority Data
Nov. 30, 2007 (JP) .................................. 2007-310462

(51) Int. Cl.
*G01N 21/35* (2006.01)
(52) U.S. Cl. .................................................... 250/341.1
(58) Field of Classification Search ................. 250/341.1
See application file for complete search history.

(56) References Cited

U.S. PATENT DOCUMENTS

| | | |
|---|---|---|
| 6,448,553 B1 | 9/2002 | Itsuji et al. |
| 6,573,737 B1 | 6/2003 | Lyon et al. |
| 6,835,925 B2 | 12/2004 | Itsuji et al. |
| 7,248,995 B2 | 7/2007 | Itsuji et al. |
| 7,358,918 B2 | 4/2008 | Itsuji |
| 7,386,024 B2 | 6/2008 | Sekiguchi et al. |
| 7,463,104 B2 | 12/2008 | Sekiguchi et al. |
| 7,542,000 B2 | 6/2009 | Itsuji |
| 7,557,588 B2 | 7/2009 | Ouchi et al. |
| 7,560,695 B2 | 7/2009 | Kasai et al. |
| 7,564,034 B2 | 7/2009 | Ouchi |
| 7,570,216 B2 | 8/2009 | Itsuji |

(Continued)

FOREIGN PATENT DOCUMENTS
EP 2031374 A2 3/2009
(Continued)

OTHER PUBLICATIONS

International Preliminary Report on Patentability dated Jun. 2, 2010 in corresponding PCT Application No. PCT/JP2008/071993.

(Continued)

*Primary Examiner* — Constantine Hannaher
(74) *Attorney, Agent, or Firm* — Fitzpatrick, Cella, Harper & Scinto

(57) ABSTRACT

An apparatus for acquiring information on a time waveform of a terahertz wave is comprised of a terahertz wave-generating unit, a waveform information-detecting unit, and a delay unit for changing the time after the terahertz wave is generated in the generating unit until it is detected as waveform information of the terahertz wave in the detecting unit, wherein the delay unit is configured so as to change a propagating distance of the terahertz wave generated by the generating unit, and associates waveform information of the terahertz wave, which is detected in the detecting unit, and the propagating distance every terahertz wave generated by the generating unit.

11 Claims, 18 Drawing Sheets

U.S. PATENT DOCUMENTS

| | | |
|---|---|---|
| 7,630,588 B2 | 12/2009 | Ouchi |
| 7,633,299 B2 | 12/2009 | Itsuji |
| 7,681,434 B2 | 3/2010 | Ouchi |
| 7,683,778 B2 | 3/2010 | Ouchi |
| 7,684,455 B2 | 3/2010 | Ouchi et al. |
| 7,688,078 B2 | 3/2010 | Miyazaki et al. |
| 7,689,070 B2 | 3/2010 | Ouchi |
| 7,701,587 B2 | 4/2010 | Shioda et al. |
| 7,709,797 B2 | 5/2010 | Sekiguchi et al. |
| 2006/0214176 A1 | 9/2006 | Ouchi et al. |
| 2007/0030115 A1 | 2/2007 | Itsuji et al. |
| 2007/0229094 A1 | 10/2007 | Kasai et al. |
| 2008/0315098 A1 | 12/2008 | Itsuji |
| 2009/0056455 A1 | 3/2009 | Ouchi |
| 2009/0059226 A1 | 3/2009 | Kajiki et al. |
| 2009/0146084 A1 | 6/2009 | Itsuji |
| 2009/0189078 A1 | 7/2009 | Itsuji |
| 2009/0198466 A1 | 8/2009 | Kajiki et al. |
| 2009/0201030 A1 | 8/2009 | Ouchi et al. |
| 2009/0213880 A1 | 8/2009 | Ouchi et al. |
| 2009/0236529 A1 | 9/2009 | Kasai et al. |
| 2009/0267858 A1 | 10/2009 | Itsuji |
| 2010/0052083 A1 | 3/2010 | Kasai |
| 2010/0140481 A1 | 6/2010 | Ouchi |
| 2010/0164636 A1 | 7/2010 | Sekiguchi et al. |
| 2010/0171835 A1 | 7/2010 | Kasai et al. |

FOREIGN PATENT DOCUMENTS

| | | |
|---|---|---|
| JP | 2003005238 A * | 1/2003 |
| JP | 2007-292701 | 11/2007 |
| WO | 2004/048945 A1 | 6/2004 |
| WO | 2006/019776 A2 | 2/2006 |
| WO | 2006/101756 A1 | 9/2006 |

OTHER PUBLICATIONS

U.S. Appl. No. 12/680,889, filed Mar. 30, 2010, Applicants: Takeaki Itsuji and Shintaro Kasai.

U.S. Appl. No. 12/742,905, filed May 13, 2010, Applicants: Takashi Katagiri and Takeaki Itsuji.

Nagel, et al., "A functionalized THz sensor for marker-free DNA analysis", Physics in Medicine and Biology, Institute of Physics Publishing, Phys. Med. Biol. 48 (2003), pp. 3625-3636.

Wachter, et al., "Metallic slit waveguide for dispersion-free low-loss terahertz signal transmission", Applied Physics Letters 90, 061111 (2007).

* cited by examiner

POSITION IRRADIATED WITH
PUMPING LIGHT x1

POSITION IRRADIATED WITH
PUMPING LIGHT x2

POSITION IRRADIATED WITH
PUMPING LIGHT x3

US 8,344,324 B2

INSPECTION APPARATUS AND INSPECTION METHOD USING ELECTROMAGNETIC WAVE

TECHNICAL FIELD

The present invention relates to an apparatus for acquiring information on a time waveform of a terahertz wave, an inspection apparatus and an inspection method for acquiring information on a sample (test object) using an electromagnetic wave, and the like. In particular, it relates to an inspection apparatus, an inspection method, and the like for acquiring information on a sample using an electromagnetic wave (in this description, it is called a terahertz wave) in a frequency domain of 30 GHz to 30 THz inclusive.

BACKGROUND ART

Recently, engineering development using a terahertz wave is prosperous. In particular, substances can be analyzed using spectra in a frequency band of 30 GHz to 30 THz inclusive which are obtained by a spectrophotometrical method.

In such a technical situation, a technique of performing a DNA analysis using that a terahertz wave propagation characteristic of a transmission line changes by producing the terahertz wave transmission line on a substrate, and dropping and drying a DNA aqueous solution on the transmission line is disclosed in Phys. Med. Biol. 48, 3625 (2003) (hereinafter referred to as "non-patent document 1"). In non-patent document 1, it is used that values of a dielectric constant to a terahertz wave differ between a single strand DNA and a double strand DNA. Thereby, it can be inspected from difference between propagation characteristics of a terahertz wave whether a DNA is a single strand or a double strand.

As mentioned above, analysis, detection, identification, and the like of a substance can be performed using a terahertz wave by obtaining optical characteristics, such as an absorption coefficient, and a complex refractive index of the substance, from a change of a propagating state.

By the way, in the method of non-patent document 1, time delay is generated using a return optical system and a Littrow reflector. A time waveform of a propagating terahertz wave can be obtained by this time delay.

Generally, measurement of a terahertz wave is performed by acquiring a time waveform of the terahertz wave by terahertz time domain spectroscopy. Heretofore, a unit of changing an optical path length of probe light propagating is used. Thereby, timing of detecting a terahertz wave in the detecting unit (the detecting unit is irradiated with a pulse-like laser beam (probe light)) can be changed (time delayed). At this time, timing of arriving at the detecting unit (generated in the generating unit) is constant.

DISCLOSURE OF THE INVENTION

In the method of non-patent document 1, since a return optical system and a Littrow reflector are used, even if an inspection element is small, a whole inspection apparatus which makes this inspection element drive may become large.

The present invention provides an apparatus for performing terahertz time domain spectroscopy by a method different from conventional art, and acquiring information on a time waveform of a terahertz wave.

The present invention is directed to an apparatus for acquiring information on a time waveform of a terahertz wave, characterized by having: a generating unit for generating a terahertz wave; a detecting unit for detecting waveform information of the terahertz wave; and a delay unit for changing the time after the terahertz wave is generated in the generating unit until it is detected as waveform information of the terahertz wave in the detecting unit, and in that the delay unit is configured so as to change a propagating distance of the terahertz wave generated by the generating unit, and associates waveform information of the terahertz wave, which is detected in the detecting unit, and the propagating distance every terahertz wave generated by the generating unit.

The apparatus can be characterized in that the generating unit is configured to include a first position which a terahertz wave generates; that the detecting unit is configured to include a second position from which waveform information of a terahertz wave is detected; that the delay unit is a distance changing unit for changing a relative position between the first position and the second position; and that the relative position between the first position and the second position determines the propagating distance.

The apparatus can be characterized in that the distance changing unit is a variable angle mirror for changing an incident angle of excitation light which is irradiated in the first position or the second position, or a movable stage for changing a relative position between the generating unit and the detecting unit.

The apparatus can be characterized by having a propagating unit for making a terahertz wave generated by the generating unit propagate, and in that the propagating unit is arranged so that a terahertz wave generated in the first position may propagate in the propagation unit and may be detected in the second position; and that the distance changing unit is the variable angle mirror.

The apparatus can be characterized by having a moving parabolic mirror for making a terahertz wave generated by the generating unit propagate in the detecting unit, and in that the distance changing unit is the variable angle mirror; and that the variable angle mirror and the moving parabolic mirror are operated with being associated.

The apparatus can be characterized in that a ratio between a pulse frequency which determines timing of generating a pulse of a terahertz wave from the first position, and a sampling frequency which determines timing of detecting waveform information of a terahertz wave in the second position is n:1 (n is a natural number of one or more).

The present invention is directed to an inspection apparatus which has: a generating unit for generating an electromagnetic wave; a detecting unit for detecting the electromagnetic wave; a propagating unit for propagating an electromagnetic wave generated in the generating unit to the detecting unit; a distance changing unit for changing a propagating distance of an electromagnetic wave through the propagating unit between an electromagnetic wave generating position of the generating unit which generates an electromagnetic wave, and an electromagnetic wave detecting position of the detecting unit which detects an electromagnetic wave; and a processing unit for associating change information of the propagating distance, and information on an electromagnetic wave detected in the detecting unit to acquire at least a part of a time waveform of the electromagnetic wave which propagates through the propagating unit, and which is an inspection apparatus which acquires information on a sample placed between the electromagnetic wave generating position and the electromagnetic wave detecting position from a change of a propagating state of the electromagnetic wave, characterized in that a ratio between a pulse frequency of an electromagnetic wave generated in the electromagnetic wave generating position, and a sampling frequency which fetches the electromagnetic wave propagating in the electromagnetic wave detecting position is n:1 (n is a natural number of one or more).

The inspection apparatus can be characterized in that at least one side of the generating unit and the detecting unit has a photoconducting unit for generating or detecting the electromagnetic wave; that the photoconducting unit is configured to include two or more electrodes and a semiconductor film which has photoconductivity; that the two or more electrodes of the photoconducting unit do not contact mutually, and are formed in contact with the semiconductor film; that a laser beam at the pulse frequency or the sampling frequency is irradiated in the electromagnetic wave generating position or the electromagnetic wave detecting position on the photoconductive film, and generation or detection of the electromagnetic wave is performed; and that the distance changing unit changes at least one side of the electromagnetic wave generating position and the electromagnetic wave detecting position to change the propagating distance.

The inspection apparatus can be characterized in that a position in which the laser beam is irradiated is a position in which charge carriers which are generated in the semiconductor film by irradiation of the laser beam can be conducted between the two or more electrodes.

The inspection apparatus can be characterized in that the distance changing unit changes an angle of a mirror provided in order to enter the laser beam into the photoconductive film to change the electromagnetic wave generating position or the electromagnetic wave detecting position; and that the processing unit receives information on an angle of the mirror to obtain change information of the propagating distance.

The inspection apparatus can be characterized in that the distance changing unit changes the electromagnetic wave generating position or the electromagnetic wave detecting position using an acoustooptic device which the laser beam passes; and that the processing unit receives information on an operating frequency of the acoustooptic device to obtain change information of the propagating distance.

The inspection apparatus can be characterized in that the distance changing unit switches the laser beam branched into two or more by opening/closing of a shutter, irradiates the electromagnetic wave generating position or the electromagnetic wave detecting position with it, and changes the electromagnetic wave generating position or the electromagnetic wave detecting position; and that the processing unit receives information on switching of the laser beam to obtain change information of the propagating distance.

The present invention is directed to an inspection element which has: a generating unit for generating an electromagnetic wave; a detecting unit for detecting the electromagnetic wave; and a propagating unit for propagating an electromagnetic wave generated in the generating unit to the detecting unit, and acquires information on a sample put on the propagating unit from a change of a propagating state of the electromagnetic wave, characterized in that at least one side of the generating unit and the detecting unit has a photoconducting unit for generating or detecting an electromagnetic wave; that the photoconducting unit is configured to include two or more electrodes, including a first electrode and a second electrode, and a semiconductor film which has photoconductivity; that the two or more electrodes of the photoconducting unit which includes the first electrode and the second electrode do not contact mutually, and are formed in contact with the semiconductor film; that the propagating unit is configured to include the first electrode, the second electrode, and a dielectric; that a laser beam is irradiated in an electromagnetic wave generating position or an electromagnetic wave detecting position on the photoconduction film, and generation or detection of an electromagnetic wave is performed; and that one or more reflecting units whose reflectances to the laser beam are different from that of the semiconductor film are provided along any of the two or more electrodes on the semiconductor film.

The present invention is directed to a method for acquiring information on a time waveform of a terahertz wave comprising the steps of: making a terahertz wave propagate; acquiring waveform information of a terahertz wave propagating in a first propagating distance; changes a propagating distance of the terahertz wave to a second propagating distance; acquiring waveform information of a terahertz wave propagating in the second propagating distance; and acquiring information on a time waveform acquired from waveform information of a terahertz wave propagating in the first propagating distance and the second propagating distance.

The present invention is directed to an inspection method comprising the steps of: generating an electromagnetic wave; detecting the electromagnetic waves; changing a propagating distance of an electromagnetic wave between an electromagnetic wave generating position where the electromagnetic wave is generated, and an electromagnetic wave detecting position where the electromagnetic wave is detected; associating change information of the propagating distance, and information on the electromagnetic wave detected to acquire at least a part of a time waveform of an electromagnetic wave propagating to the electromagnetic wave detecting position, and acquires information on a sample placed between the electromagnetic wave generating position and the electromagnetic wave detecting position from a change of a propagating state of the electromagnetic wave, characterized in that a ratio between a pulse frequency of an electromagnetic wave generated in the electromagnetic wave generating position, and a sampling frequency which fetches the electromagnetic wave propagating in the electromagnetic wave detecting position is set at n:1 (n is a natural number of one or more).

The inspection method can be characterized in that, at the generating step, the electromagnetic wave generating position is a position where a laser beam is irradiated for an electromagnetic wave at the pulse frequency to be generated, and an electromagnetic waves which is generated in the electromagnetic wave generating position is modulated by a position of irradiation of the laser beam being changed; and that at the detecting step, synchronous detection of the modulated electromagnetic wave is performed.

The present invention is directed to a terahertz time domain spectroscopy comprised of the steps of generating a terahertz wave, propagating the generated terahertz wave, detecting information on the propagated terahertz wave, and configuring a time waveform of a terahertz wave from information on the detected terahertz wave, wherein a propagating distance of a terahertz wave is changed in order to obtain the time waveform.

An apparatus for acquiring information on a time waveform of a terahertz wave which relates to the present invention associates waveform information of a terahertz wave, which is detected in the detecting unit, and the propagating distance every terahertz wave which is generated by the generating unit. Thereby, in order to obtain a time waveform of a terahertz wave, a method of changing a propagating distance of the terahertz wave can be provided.

Further features of the present invention will become apparent from the following description of exemplary embodiments with reference to the attached drawings.

BEST MODE FOR CARRYING OUT THE INVENTION

Figure 1A:
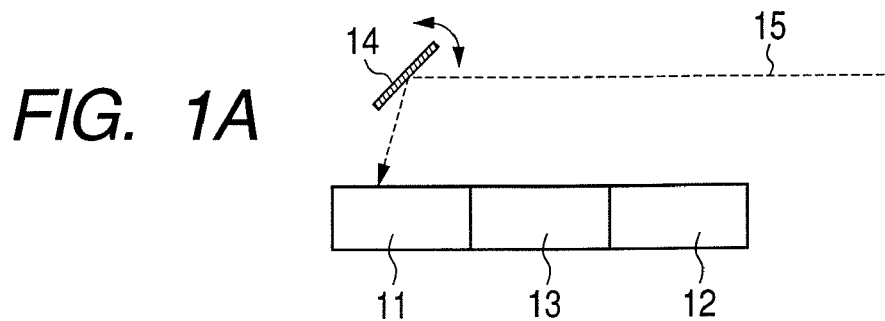
FIGS. 1A, 1B, 1C and 1D are schematic diagrams for describing an apparatus for acquiring information on a time waveform of a terahertz wave which relates to this embodiment.

An apparatus (or A waveform information acquisition apparatus) for acquiring information on a time waveform of a terahertz wave which relates to this embodiment will be described using FIG. 1A.

First, reference numeral 11 denotes a generating unit for generating a terahertz wave. It is desirable that the above-mentioned generating unit 11 is a semiconductor which has photoconductivity (this is also called single layer structure and a photoconduction film) such as low-temperature grown GaAs (LT-GaAs), InGaAs, and AlGaAs. In addition, it is desirable that the above-mentioned generating unit 11 is a structure (two or more layer structure) configured to include a semiconductor which has the above-mentioned photoconductivity. The above-mentioned structure is diode structure (structure given rectification) which is configured to include a semiconductor with bandgap energy smaller than photon energy of pumping light. For example, p-i-n diode structure, metal-i-n diode structure, metal-i-metal diode structure, Schottky barrier diode structure, and the like can be used. These can make small each current, which flows by carriers which are generated with radiation of pumping light, by applying a reverse bias to each element. For this reason, even if resistance of the generating unit 11 is small, an electric field can be efficiently applied to carriers. Here, although InGaAs or the like whose resistance is lower than that of, for example, LT-GaAs can be used as a material of an i layer, the present invention is not limited to this. In addition, a resonant tunneling diode, a semiconductor superlattice, a superconductor, or the like can be used in the above-mentioned generating unit 11.

Next, reference numeral 12 denotes a detecting unit for detecting waveform information of a terahertz wave. Configuration of the above-mentioned detecting unit 12 can be considered to be the same as that of the above-mentioned generating unit 11.

Here, the waveform information of a terahertz wave is, for example, a value of an amplitude in a certain time on a time waveform (a wave form of the terahertz wave making a time-axis a horizontal axis). In addition, the above-mentioned waveform information may be at least part information of the waveform.

In addition, reference numeral 14 denotes a delay unit for changing time after a terahertz wave is generated in the above-mentioned generating unit 11 until it is detected as waveform information of the terahertz wave in the above-mentioned detecting unit 12. The above-mentioned delay unit 14 is a mechanism for performing terahertz time domain spectroscopy (THz-TDS) mentioned above. Although specific configuration of the delay unit 14 will be mentioned later, reference numeral 14 in FIG. 1A denotes a variable angle mirror.

Then, the above-mentioned delay unit 14 is configured so as to change a propagating distance of the terahertz wave generated by the above-mentioned generating unit 11. Here, the above-mentioned propagating distance is a distance propagating after a terahertz wave is generated in the above-mentioned generating unit 11 until it is detected in the above-mentioned detecting unit 12.

Furthermore, waveform information of a terahertz wave which is detected in the above-mentioned detecting unit 12, and the above-mentioned propagating distance are associated every terahertz wave (or a different terahertz wave) which is generated by the above-mentioned generating unit 11. In addition, the different terahertz wave means to be a relation between a first terahertz wave and a second terahertz wave, which differs from the first terahertz wave, among terahertz waves generated by the above-mentioned generating unit 11.

Thereby, terahertz time domain spectroscopy is performed by a method different from conventional art, and information on a time waveform of a terahertz wave can be acquired. In addition, the information on the above-mentioned time waveform also includes information on an amplitude and a phase of a terahertz wave, and the like.

Here, the terahertz time domain spectroscopy is a method of configuring a time waveform of a terahertz waveform information on the above-mentioned detected terahertz wave. This embodiment is a method performed by changing a propagating distance of a terahertz wave in order to obtain the above-mentioned time waveform.

(Delay Unit)

Next, the above-mentioned delay unit 14 will be described using FIG. 1B.

The above-mentioned delay unit 14 can have a function of changing a relative position between a position (it is also called a first position 17) in which a terahertz wave is generated by the above-mentioned generating unit 11, and a position (it is also called a second position 18) in which waveform information of the terahertz wave is detected by the above-mentioned detecting unit 12. Anything is sufficient so long as it (it is also called a distance changing unit) changes a distance between the above-mentioned first position 17 and the above-mentioned second position 18.

Figure 1B:
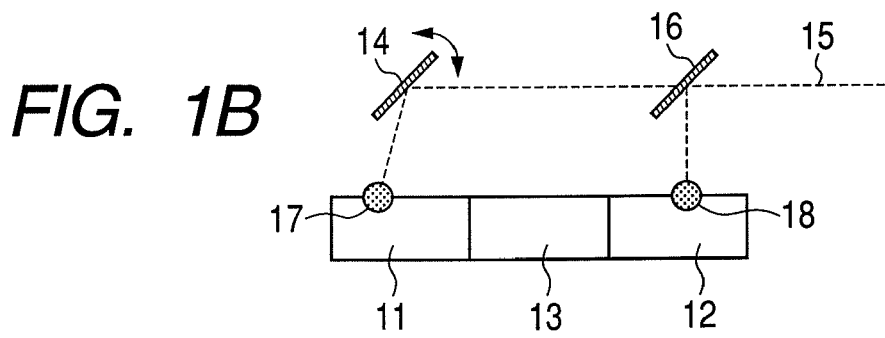

In FIGS. 1A and 1B, the above-mentioned distance changing unit (or the above-mentioned delay unit 14) is a variable angle mirror for changing an incident angle of an excitation light 15 with which the above-mentioned first position 17 is irradiated. In addition, the above-mentioned incident angle is an angle at which the above-mentioned excitation light 15 is incident into the above-mentioned variable angle mirror. In addition, it can be also said that the above-mentioned variable angle mirror has a function of the above-mentioned excitation light 15 changing a reflection angle on the above-mentioned variable angle mirror.

Figure 1C:
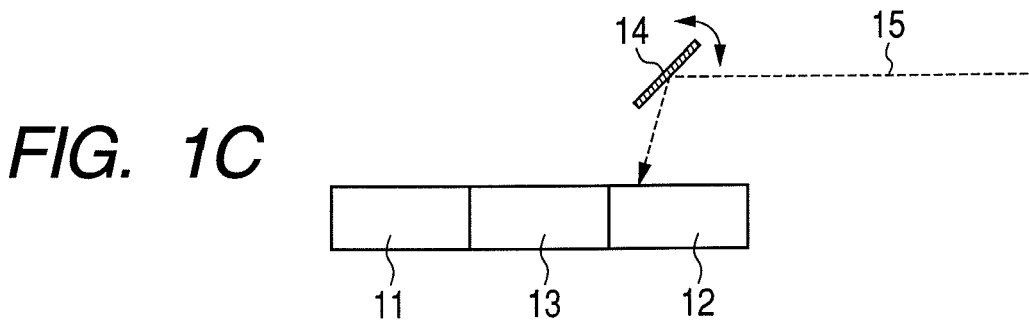

At this time, as illustrated in FIG. 1B, a fixed mirror 16 (half-mirror) can be arranged so that the above-mentioned excitation light 15 may be divided and irradiated on the above-mentioned second position 18 and the above-mentioned variable angle mirror. In addition, as illustrated in FIG. 1C, the above-mentioned variable angle mirror (or the above-mentioned delay unit 14) may be arranged so that an angle of the excitation light 15 with which the above-mentioned second position 18 is irradiated may be changed.

In addition, reference numeral 13 denotes a propagating unit through which a terahertz wave propagates, and is a region through which the terahertz wave propagates. As the above-mentioned propagating unit 13, there are, for example, a transmission line (microstrip line) which is configured to include a strip-shaped electrode, and the like. Furthermore, the propagating unit 13 may include air (clearance) through which a terahertz wave propagates. Nevertheless, the present invention is not limited to these.

Figure 1D:
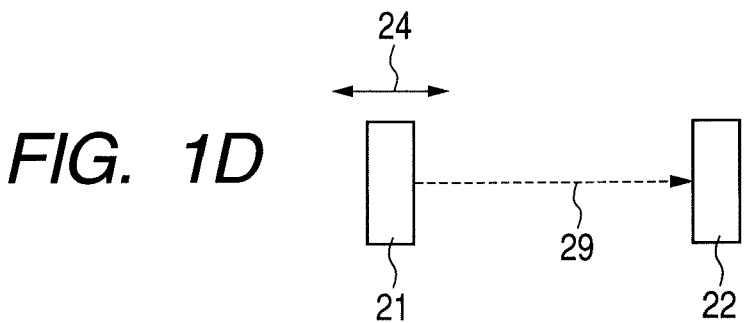

Furthermore, in FIG. 1D, the above-mentioned distance changing unit (or the above-mentioned delay unit 14) is a movable stage for changing a relative position between the above-mentioned generating unit 11 and the above-mentioned detecting unit 12. It is also good to perform configuration so as to change a position of the above-mentioned generating unit 11 to the above-mentioned detecting unit 12. In addition, it is also good to perform configuration so as to change a position of the above-mentioned detecting unit 12 to the above-mentioned generating unit 11. In addition, reference numeral 29 denotes a terahertz wave which propagates in a space, such as air. Nevertheless, the present invention is not limited to these.

In addition, it can be also configured to use together a moving parabolic mirror for making the above-mentioned detecting unit 12 propagate a terahertz wave generated by the above-mentioned generating unit, using the above-mentioned variable angle mirror as the above-mentioned distance changing unit (or the above-mentioned delay unit 14). At this time, it is sufficient to operate the above-mentioned variable angle mirror and the above-mentioned moving parabolic mirror with associating them. This will be described in full detail in examples.

Here, the above-mentioned generating unit 11 is configured to include a first position in which a terahertz wave is generated. In addition, the above-mentioned detecting unit 12 is configured to include a second position in which waveform information of a terahertz wave is detected.

Thereby, the above-mentioned propagating distance can be determined with a relative position between the above-mentioned first position and the above-mentioned second position.

In addition, in terahertz time domain spectroscopy, it is sufficient that a ratio of a pulse frequency to a sampling frequency is n:1 (n is a natural number of one or more). Here, timing when a pulse of a terahertz wave is generated from the above-mentioned first position is determined by the pulse frequency. In addition, timing when waveform information of a terahertz wave is detected in the above-mentioned second position is determined by the sampling frequency. This will be mentioned later.

(Method)

A method (or a waveform information acquisition method) for acquiring information on a time waveform of a terahertz wave which relates to this another example has the following steps.

1) A step of making a terahertz wave propagates.
2) A step of acquiring waveform information of the terahertz wave which propagates in a first propagating distance.
3) A step of changing the propagating distance of the above-mentioned terahertz wave into a second propagating distance.
4) A step of acquiring waveform information of the terahertz wave which propagates in the above-mentioned second propagating distance.
5) A step of acquiring information on a time waveform acquired from the waveform information of the terahertz wave propagating in the above-mentioned first propagating distance and the above-mentioned second propagating distance.

In addition, as for the information on the above-mentioned time waveform, it is also sufficient to configure a whole time waveform from the above-mentioned waveform information. In addition, as for the information on the above-mentioned time waveform, it is also sufficient to configure a whole time waveform from several information on a time waveform. Furthermore, it is also sufficient not to configure a time waveform.

(Inspection Apparatus)

The inspection apparatus and inspection method which relate to this embodiment have the following fundamental components or steps, in order to achieve the above-mentioned advantageous effects. That is, the inspection apparatus has a propagating unit for propagating an electromagnetic wave generated in a generating unit to a detecting unit, and changes a propagating distance of the above-mentioned electromagnetic wave between an electromagnetic wave generating position of the above-mentioned generating unit in which the electromagnetic wave is generated, and an electromagnetic wave detecting position of the above-mentioned detecting unit in which the electromagnetic wave is detected, by a distance changing unit. In addition, the inspection method includes generating an electromagnetic wave, detecting the above-mentioned electromagnetic wave, and changing a propagating distance of an electromagnetic wave between an electromagnetic wave generating position in which the above-mentioned electromagnetic wave is generated, and an electromagnetic wave detecting position in which the above-mentioned electromagnetic wave is detected.

In the above-mentioned basic configuration, with associating information on a change of the above-mentioned propagating distance and information on the above-mentioned electromagnetic wave detected by a processing unit, at least a part of time waveform of the electromagnetic wave propagated in the above-mentioned electromagnetic wave detecting position is acquired. In this way, information on a sample placed between the above-mentioned electromagnetic wave generating position and the above-mentioned electromagnetic wave detecting position is acquired from a change of a propagating state of the above-mentioned electromagnetic wave. Here, in order to acquire the above-mentioned time waveform, a ratio between a pulse frequency of an electromagnetic wave in the electromagnetic wave generating position, and a sampling frequency which fetches the electromagnetic wave propagating in the electromagnetic wave detecting position is n:1 (n is a natural number of one or more). Typically, the pulse frequency and sampling frequency coincide. Furthermore, here, a duration of pulses of an electromagnetic wave generated in the generating unit is larger enough than a duration of the above-mentioned sampling, and it is set so that generation and sampling of an electromagnetic pulse may be performed almost simultaneously. Although the above-mentioned advantageous effects are achieved by a configuration of changing a propagating distance of the above-mentioned electromagnetic wave by the above-mentioned distance changing unit or steps, various aspects as illustrated below are possible within a range of the above-mentioned basic configurations.

In embodiments and examples which are mentioned later, generation of the above-mentioned electromagnetic pulse is performed by performing excitation optically by a pumping beam using a photoconductive semiconductor switch element, and the above-mentioned sampling is performed by performing gating optically by probe light. However, otherwise, electromagnetic waves can be also generated using semiconductor devices, such as an electrooptical crystal, a semiconductor crystal, a resonant tunneling diode, and a Gunn diode. In addition, sampling and fetching an electromagnetic wave can be also performed using a sampling method using a Pockels effect of an electrooptic effect, and detection elements, such as a Schottky barrier diode.

In addition, the above-mentioned propagating unit may be a portion including a space besides a transmission line mentioned later. In such a case, for example, an electromagnetic wave is emitted to a space from the generating unit by an antenna, and an electromagnetic wave is fetched by an antenna in the detecting unit. In addition, in the case of a transmission line, a sample is placed on the transmission line, but, in the case of a space, for example, it is held in a holding part in the space.

In addition, in embodiments and examples which are mentioned later, at least one side of an electromagnetic wave generating position and an electromagnetic wave detecting position is changed, and a propagating distance of the above-mentioned electromagnetic wave is changed. However, for example, when the above-mentioned propagating unit includes a space, the generating unit or detecting unit itself can be moved by a spatial distance changing unit, and a propagating distance can be also changed.

Hereafter, forms for performing the present invention will be described with referring to drawings. An inspection apparatus is made of a device (inspection element) used for inspection, and a drive system which drives the device. A top view and a sectional view (cuts by line 2B-2B) of a device main part and a part of a drive system are described in FIGS. 2A and 2B. In addition, all of the device and drive system are described in FIG. 2C.

(Device)

Figure 2A:
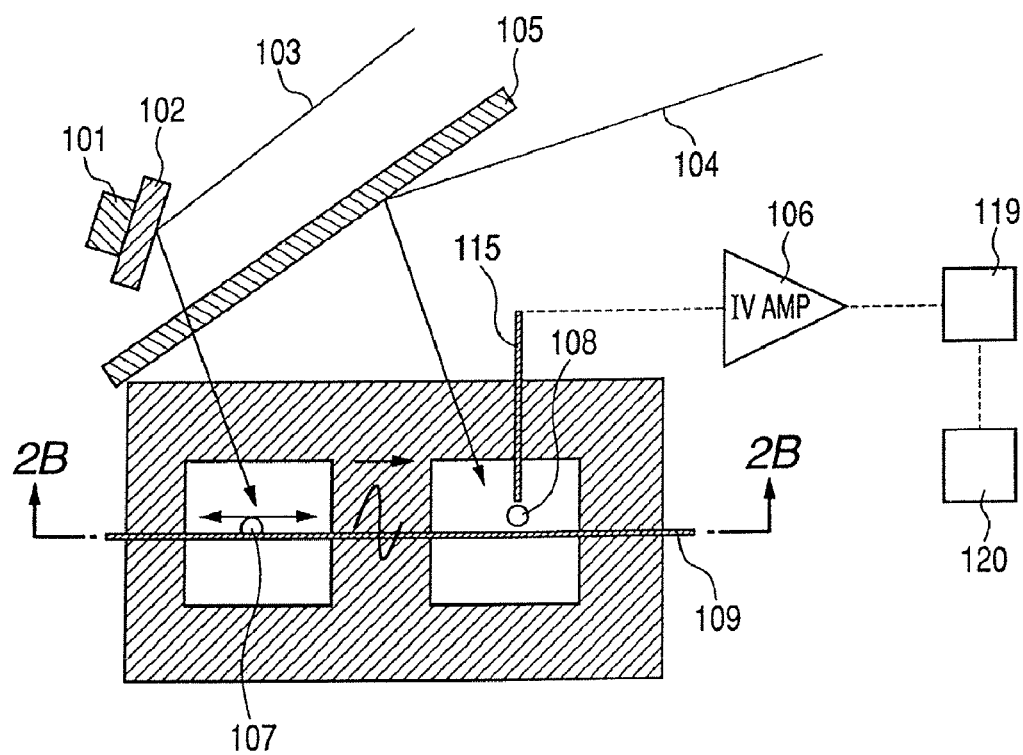
FIGS. 2A, 2B and 2C are drawings including a drive system for describing an embodiment and a first example of an inspection apparatus and an inspection method of the present invention.
Figure 2B:
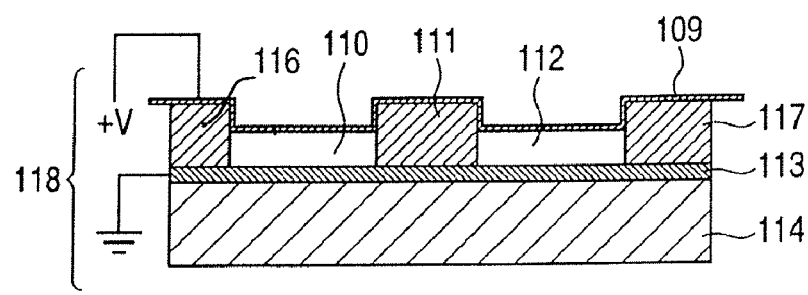

As illustrated in FIGS. 2A and 2B, the main part of this device includes a reference electrode 113, a first photoconductive film 110, a second photoconductive film 112, a first dielectric 111, a second dielectric 116, a third dielectric 117, a first electrode 109, and a second electrode 115, on a substrate 114. The reference electrode means an electrode which becomes a standard of an electric potential in an inspection element 118 used in inspection of this embodiment.

The dielectrics 111, 116, and 117 are formed so as to surround the first and second photoconductive films 110 and 112. Suppose that a dielectric of a portion between the first and second photoconductive films 110 and 112 is called a first dielectric 111 for convenience in this embodiment. In addition, in FIG. 2B, suppose that a dielectric of a portion in a left side of the first photoconductive film 110 is called a second dielectric 116, and a dielectric of a portion in a right side of the second photoconductive film 112 is called a third dielectric 117. Nevertheless, suppose here that the first, second, and third dielectrics 111, 116, and 117 are not isolated with clear limits but that they are united.

The first electrode 109 is formed on a top face of the first, second, third dielectrics 111, 116, and 117 and the first, and second photoconductive films 110 and 112. The second electrode 115 is formed so as to have an end on the second photoconductive film 112 and not to intersect with the first electrode 109.

The above is a configuration of the device main part used for this inspection apparatus. A part of the first photoconductive film 110 is the above-mentioned generating unit, a part of the second photoconductive film 112 is the above-mentioned detecting unit, and a part of first dielectric 111 and a part of the first and second photoconductive films 110 and 112 adjacent to the first dielectric 111 are the above-mentioned propagating unit.

(Drive system)

Next, the drive system and driving method which make this device drive will be described. The reference electrode 113 is grounded electrically and a bias voltage (approximately 10 V) is applied to the first electrode 109. In addition, a high gain current-voltage conversion amplifier 106 is connected to the second electrode 115.

Figure 2C:
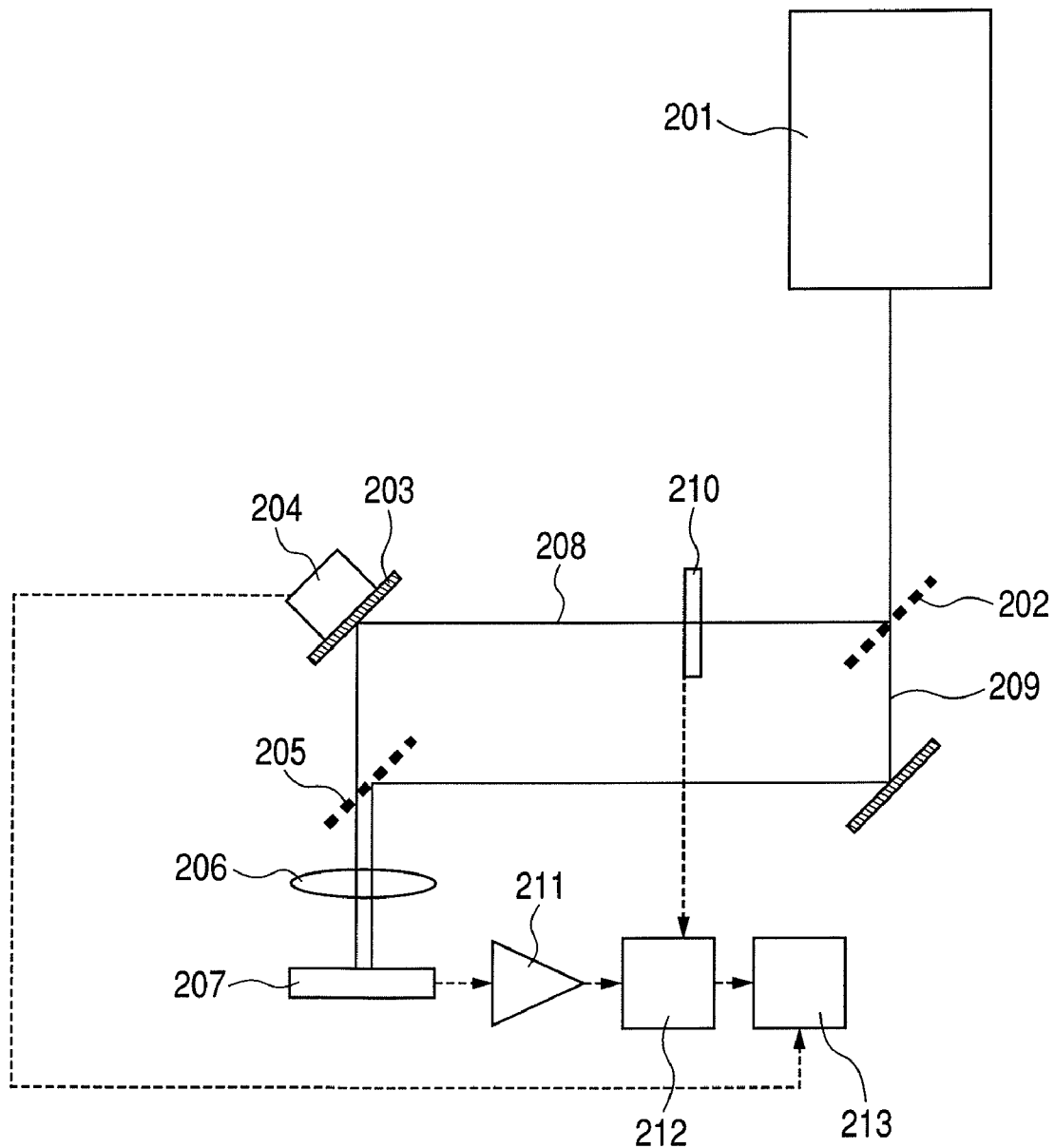

On the other hand, in the drive system in FIG. 2C, a laser beam emitted from a laser light source 201 is divided by a beam splitter 202. As the laser light source 201, for example, a modelocked titanium sapphire laser is used, and a so-called ultrashort pulse laser beam whose pulse time width is approximately 100 femtoseconds is used as a laser beam. Let a laser beam, reflected by the beam splitter 202 among laser beams divided by the beam splitter 202, be called pumping light 208, and let a laser beam, which permeates the beam splitter 202, be called probe light 209. In addition, in FIGS. 2A to 2C, a laser beam is drawn by a continuous line and a flow of an electric signal is drawn by a dotted line. In addition, a mirror is drawn by a thick continuous line, and a beam splitter is drawn by a thick dotted line, respectively.

Pumping light 208 is bent for an optical path through an optical chopper 210 by a pumping light side mirror 203 in which an actuator 204 is installed, and is incident into a device 207 through a lens 206. Here, the device 207 drawn in FIG. 2C is the same as a device 118 described in detail in FIGS. 2A and 2B. In addition, similarly, the probe light 209 is also bent for an optical path by a probe light side mirror 205, and is incident into the device 207 through the lens 206. In order to make optical axes of the pumping light 208 and probe light 209 approach, a translucent mirror is used for the probe light side mirror 205 for a part of the pumping light 208 to be able to permeate it. For this reason, a thick dotted line shows the probe light side mirror 205. An optical path length from the beam splitter 202 to the device 207 is adjusted so as to be approximately equal for the pumping light 208 and probe light 209. That is, it is made that the pumping light 208 and the probe light 209 irradiate respective predetermined positions almost simultaneously. More strictly, the optical path length is adjusted so that the probe light 209 may be irradiated on the predetermined position at the same time as a part of an electromagnetic wave generated by radiation of the pumping light 208 arrives at a position irradiated with the probe light 209.

The pumping light side mirror 203, probe light side mirror 205, and actuator 204 which are illustrated in FIG. 2C are the same ones respectively as the pumping light side mirror 102, probe light side mirror 105, and actuator 101 which are illustrated in FIG. 2A. As for arrangement of the mirror 102 and actuator 101 in FIG. 2A, arrangement in FIG. 2C better expresses actual arrangement. In addition, in order to avoid becoming complicated, the lens 206 illustrated in FIG. 2C is not necessarily required as not drawn in FIGS. 2A and 2B. In FIG. 2A, reference numeral 103 denotes pumping light and reference numeral 104 denotes probe light.

The probe light 104 is convergently irradiated in a position 108 irradiated with the probe light on the device 118. The position 108 irradiated with the probe light is the above-mentioned electromagnetic wave detecting position, and is made to be a clearance between the first electrode 109 and second electrode 115. In addition, the pumping light 103 is convergently irradiated in a position 107 irradiated with the pumping light on the device 118. The position 107 irradiated with the pumping light is the above-mentioned electromagnetic wave generating position, and is in the vicinity of the first electrode 109 and on the first photoconductive film 110. The vicinity described here means nearness to such an extent that photo carriers generated in the first optical semiconductor film 110 with the pumping light 107 are accelerated by an electric field between the first electrode 109 and reference electrode 113. That is, it is a distance of such nearness that the generated charge carriers conduct between both electrodes, and a current occurs. Typically, the position 107 irradiated with the pumping light is within three times of a width of the first electrode from an edge of the first electrode 109.

In this way, when the pumping light 103 arrives at the position 107 irradiated with the pumping light, photo carriers are generated in the first photoconductive film 110. The generated photo carriers are accelerated by the electric field between the first electrode 109 and reference electrode 113. An electromagnetic wave occurs by the above-mentioned photo carriers being accelerated. Here, since a frequency of this electromagnetic wave is within the range of 30 GHz to 30 THz, it is also henceforth called a terahertz wave.

The above-mentioned terahertz wave occurred propagates in a microstrip line of transmission line which includes the first electrode 109, reference electrode 113, and first photoconductive film 110. Furthermore, the terahertz wave is propagated into the microstrip line of transmission line which includes the first electrode 109, reference electrode 113, and first dielectric 111. Furthermore, the terahertz wave propagates in the microstrip line type transmission line including the first electrode 109, reference electrode 113 and second photoconductive films 112, and arrives at the position 108 irradiated with the probe light. Here, these transmission lines configure the above-mentioned propagating unit.

When a pulse of the probe light 104 arrives at the position 108 irradiated with the probe light at the same time as the above-mentioned terahertz wave arrives at the position 108 irradiated with the probe light, the followings occur. That is, photo carriers occurred in the second photoconductive film 112 by the probe light 104 are accelerated by the electric field of a terahertz wave. The accelerated photo carriers generate a current. The generated current is amplified by the amplifier 106 and is detected by a lock-in amplifier 119. At this time, synchronization is taken by inputting a reference signal of the optical chopper 210 into the lock-in amplifier 119. An output signal from the lock-in amplifier 119 is recorded by a computer 120. Here, the computer 120 configures the above-mentioned processing unit. When the signal is strong enough, the optical chopper 210 and lock-in amplifier 119 may be omitted, and it is also sufficient to record the signal of the amplifier 106 directly by the computer 120 through an AD converter and the like (not illustrated). In addition, an amplifier 211, a lock-in amplifier 212, and a computer 213 which are illustrated in FIG. 2C are the same ones as the amplifier 106, lock-in amplifier 119, and computer 120, which are illustrated in FIG. 2A, respectively.

(Acquisition of Time Waveform)

In this embodiment, an ultrashort pulse laser beam with approximately 100 femtoseconds of pulse time width as mentioned above is divided for pumping light and probe light to be obtained. Therefore, a ratio between a pulse frequency of an electromagnetic wave generated in a position irradiated with the pumping light (electromagnetic wave generating position) and a sampling frequency of fetching the electromagnetic wave propagating into a position irradiated with the probe light (electromagnetic wave detecting position) is 1:1. In addition, a duration of a pulse of an electromagnetic wave propagating into the detecting unit is larger enough than a duration of sampling by the probe light. Therefore, as mentioned later, at least a part of time waveform of an electromagnetic wave propagating into the detecting unit is acquirable.

A whole or partial image of a time waveform of a terahertz wave is acquirable by relatively shifting (generating time delay) time when the above-mentioned terahertz wave arrives at the position 108 irradiated with the probe light and time when the probe light 104 arrives at the position 108 irradiated with the probe light. In this embodiment, an angle of the pumping light side mirror 102 is changed using the actuator 101 illustrated in FIG. 2A, and a position 107 irradiated with the pumping light is moved along the first electrode 109. Thereby, a propagating distance of the above-mentioned propagating unit changes, and the time when a terahertz wave arrives at the position 108 irradiated with the probe light can be made to shift back and forth. Here, the actuator 101 configures the above-mentioned distance changing unit.

Figure 3A:
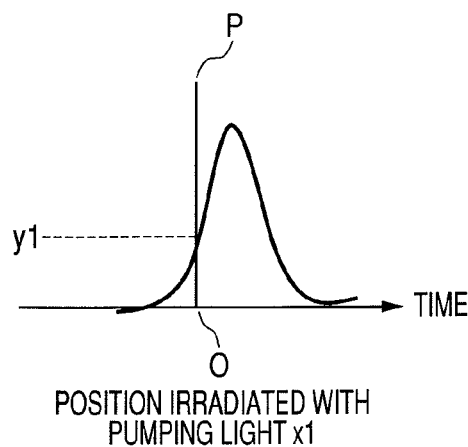
FIGS. 3A, 3B, 3C and 3D are drawings for describing a generation principle of time delay in the above-mentioned embodiment and first example.
Figure 3B:
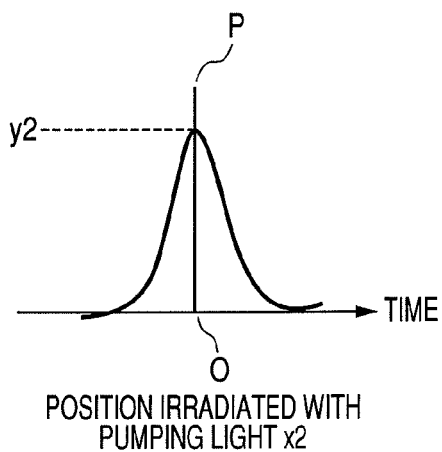
Figure 3C:
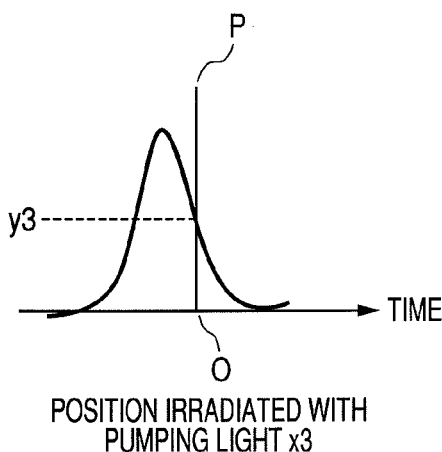

This principle is schematically illustrated in FIGS. 3A to 3D. Relative a relation between the probe light incident time and the time waveform of the above-mentioned electromagnetic wave propagating into the detecting unit at the time when the position 107 irradiated with the pumping light is x1, x2, or x3 is illustrated in FIGS. 3A, 3B and 3C. Here, the position 107 irradiated with the pumping light is made x1, x2, and x3 in order near the position irradiated with the probe light 108. Let a horizontal axis be the time and let a vertical axis be the electric field strength of a terahertz wave propagating into the detecting unit. In addition, as illustrated, let the time origin be the probe light incident time.

Figure 3D:
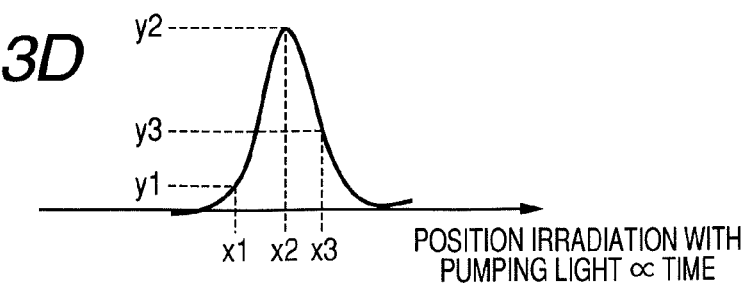

A value of a part (that is, a sampled part) in which the time waveform of the above-mentioned terahertz wave propagating into the detecting unit and the probe light incident time lap is detected by the lock-in amplifier 119. The output value obtained also changes by shifting the position 107 irradiated with the pumping light. By synthesizing FIGS. 3A, 3B and 3C, a waveform made by letting the horizontal axis be the position irradiated with the pumping light, and letting the vertical axis be the electric field strength of the above-mentioned terahertz wave propagating into the detecting unit as illustrated in FIG. 3D is obtained.

The following a relational expression holds between the position 107 irradiated with the pumping light and the actual time:

$$t = n_{MSL} x/c$$

Where, t denotes time, $n_{MSL}$, does an effective refractive index of a terahertz wave propagating a microstrip line type transmission line on a photoconductive film, x does a moving distance of the position 107 irradiated with the pumping light, and C does velocity of light. This formula shows that a time waveform can be acquired when combinations of positions irradiated with the pumping light, and output values obtained in respective irradiation positions are obtained. In this embodiment, positional information on the position 107 irradiated with the pumping light is obtained by fetching a signal from the actuator 101 into the computer 120. In this way, the computer 120 associates change information of the propagating distance, and information on an electromagnetic wave detected in the detecting unit to acquire at least a part of a time waveform of the electromagnetic wave which propagates through the propagating unit.

In this way, in this embodiment, the distance changing unit changes an angle of the mirror provided in order to enter a laser beam into the photoconductive film to change the electromagnetic wave generating position or the electromagnetic wave detecting position. The computer which is the above-mentioned processing unit receives information on the angle of the mirror to obtain change information of the propagating distance.

According to the inspection apparatus and inspection method of this embodiment, time delay of an electromagnetic wave is generated by changing an irradiation position of pumping light, and thereby a time waveform of the electromagnetic wave is acquired. For that reason, since a return optical system and a Littrow reflector become unnecessary, the whole inspection apparatus becomes small. In addition, as mentioned above, the configuration of the generating unit of an electromagnetic wave, the detecting unit of an electromagnetic wave, the processing unit, and the distance changing unit in this embodiment is an example.

In addition, the following forms are also possible. That is, the generating unit and detecting unit may be accumulated on different substrates among the embodiments described above, and a space may be used in the propagating unit instead of the microstrip line. In addition, in this case, although a terahertz wave is emitted to the space, in order to enhance coupling efficiency with the space, an antenna may be accumulated on the substrates. In addition, the present invention can be applied to a so-called terahertz time domain spectrophotometer (THz-TDS), and another form of the present invention is a terahertz time domain spectrophotometer. Specifically, it includes a terahertz wave generating unit in which a terahertz wave is generated by irradiation of pumping light, a propagation region which the generated terahertz wave propagates, and a terahertz wave detecting unit which detects the terahertz wave which propagates in the above-mentioned propagation region by radiation of probe light. Then, the propagating distance in which the above-mentioned terahertz wave propagates in the above-mentioned propagation region is changed by changing an irradiation position of the above-mentioned pumping light with fixing irradiation timing of the above-mentioned probe light. On a method of changing this propagating distance, techniques described in the following examples are applicable. By this configuration, the delay time of the above-mentioned terahertz wave which propagates in the above-mentioned propagation region can be changed, which can be replaced from a usual measurement method of specific points of time waveform pulses performed by delaying irradiation timing of probe light.

EXAMPLES

First Example

To Change Incident Angle by Variable Angle Mirror

A more specific example will be below described using numerical values.

A first example will be described using FIGS. 2A to 2C. In the first example, for the substrate 114, for example, a silicon substrate is used, and the reference electrode 113 is formed by stacking titanium and gold by a vacuum deposition method. The reference electrode 113 is made to be approximately 300 nm in thickness. Low-temperature growth gallium arsenide (LT-GaAs) films (approximately 1 to 2 μm in thickness) and the like which are given crystal growth with a molecular beam epitaxy method at 200° C. to 300° C. are used for the first photoconductive film 110 and second photoconductive film 112. A so-called epitaxial lift-off method, a method of removing a substrate by wet etching after AuSn bonding, and the like can be used for the method of installing the above-mentioned LT-GaAs films on the reference electrode 113. The first photoconductive film 110 and second photoconductive film 112 are separately installed by approximately 1 mm.

For the dielectrics 111, 116, and 117, for example, BCB (benzocyclobutene) is used. The thickness of BCB is made to be approximately 3 to 6 μm. Using the lift-off process using photography and a vacuum deposition method, titanium and gold are stacked on the photoconductive films and dielectrics, and the first electrode 109 is formed. In addition, in a similar way, the second electrode 115 is formed. The first electrode 109 and second electrode 115 are formed so as to have an approximately 10-μm clearance on the second photoconductive film 112. Each of the first and second electrodes 109 and 115 is made to be approximately 5 to 10 μm in width. The above is a specific configuration of the inspection element in this example.

Next, the setup method of the inspection element in this example will be described. The pumping light 103 is irradiated in the vicinity of the first electrode 109 (position 107 irradiated with the pumping light). The vicinity said here is a region within approximately 15 μm from an edge of the first electrode 109.

For example, when an objective lens with a focal length of 20 mm is used for the lens 206 illustrated in FIGS. 2A to 2C, a condensed position 107 of the pumping light moves by approximately 1 mm by changing an incident angle of the pumping light 103 by 2.86°. For that purpose, what is necessary is just to lean an angle of the mirror 102 for pumping light by 1.43° using the actuator 101, such as a piezo actuator. Nevertheless, this is an approximate value in the case of assuming that an objective lens with a focal length of 20 mm is a thin walled single lens.

It is known in the above-mentioned non-patent document 1 that a terahertz wave generated and propagated by this device 118 becomes a pulse form (having an approximately 1-THz band as a frequency) with a picosecond order of duration width. A refractive index of GaAs at 1 THz is approximately 3.6, and an effective refractive index in the case of using GaAs for a dielectric of a microstrip line is approximately 3 or larger (nevertheless, in the case that a GaAs film thickness is approximately 2 μm and a line width is approximately 5 μm). Therefore, when the condensed position 107 of the pumping light moves by 1 mm, this is equivalent to approximately 10 ps when converting it into propagation time of the above-mentioned terahertz wave. That is, since 10 ps of time delay is generated here by moving the position 107 irradiated with the pumping light by approximately 1 mm using the actuator 101, a most time waveform of the above-mentioned electromagnetic wave propagating into the detecting unit is acquirable.

In this example, synchronous detection is performed using the optical chopper 210 and lock-in amplifier 212. In that case, it is also good to use a method of moving it step-wise every several μm (for example, 5 μm) as a method of moving the position 107 irradiated with the pumping light along the first electrode 109. That is, a time waveform of a terahertz wave propagating into the detecting unit by repeating operations of moving it by 5 μm to acquire data, and further moving by 5 μm to acquire data, and moving it totally in approximately 1 mm of distance.

As mentioned above, in this example, it is as follows. That is, at least one side of the generating unit and detecting unit has a photoconducting unit for generating or detecting an electromagnetic wave, and the photoconducting unit is configured to include two or more electrodes and a semiconductor film which has photoconductivity. The two or more electrodes of the photoconducting unit do not contact mutually, and are formed in contact with the semiconductor film, and a laser beam at the above-mentioned pulse frequency or the above-mentioned sampling frequency is irradiated in the electromagnetic wave generating position or electromagnetic wave detecting position on the photoconductive film, and generation or detection of the electromagnetic wave is performed. In addition, the above-mentioned distance changing unit changes at least one side of the above-mentioned electromagnetic wave generating position and the above-mentioned electromagnetic wave detecting position to change the above-mentioned propagating distance.

In addition, besides this, it is also good to modulate a voltage applied to the first electrode 109 in approximately 10 kHz without using the optical chopper 210, and performing synchronous detection synchronizing with the applied voltage modulation. In this case, since the applied voltage can be given high-speed modulation, it is also good to move continuously the position 107 irradiated with the pumping light at high speed. In addition, in order to enhance a signal-to-noise ratio, it is also good to adopt a method of repeatedly perform an operation of moving the position 107 irradiated with the pumping light by approximately 1 mm, and accumulating acquired time waveforms.

An example of a sample inspection using an inspection apparatus which is made of the device and drive system of this example will be described below. A DNA aqueous solution is dropped on a part, where the first electrode 109 and first dielectric 111 lap, using a micropipette, or the like. For the DNA, for example, vector PCDNA3 (5.4 kb) is used, and 100 nl of aqueous solution with approximately 0.5 μg/μl of concentration is dropped. In addition, two types of DNA aqueous solutions, that is, a double-stranded solution and a single-stranded solution which is denaturalized in hot water are prepared. The dropped DNA aqueous solutions are dried soon and DNAs deposit. Since DNAs deposit on and near the first electrode 109, an effective refractive index of the microstrip line which includes the first dielectric 111, first electrode 109, and reference electrode 113 changes, and some 100 fs of time delay occurs on a propagating electromagnetic wave. Since amounts of generated time delay differ in single-stranded DNAs and double-stranded DNAs, it can be discriminated whether the dropped sample is the single stranded DNAs or double-stranded DNAs.

In this example, since the return optical system and Littrow reflector become unnecessary, there is an advantage that a whole apparatus becomes small. In addition, by using a mirror with an actuator for an irradiation position change of the pumping light, there is no attenuation of pumping light and alignment of a laser beam, and the like are easy.

In addition, a stroke frequency can be made quick by using a small mirror. Since an influence of noise by vibration at the time of an operation becomes large when a large-sized mechanism is operated at high speed, it is not good.

The amount of time delay described above changes with a thickness of the first dielectric 111, or a width of the first electrode 109. What is given above is only an example.

Second Example

To Change Diffraction Angle by Acoustooptic Device

Figure 4:
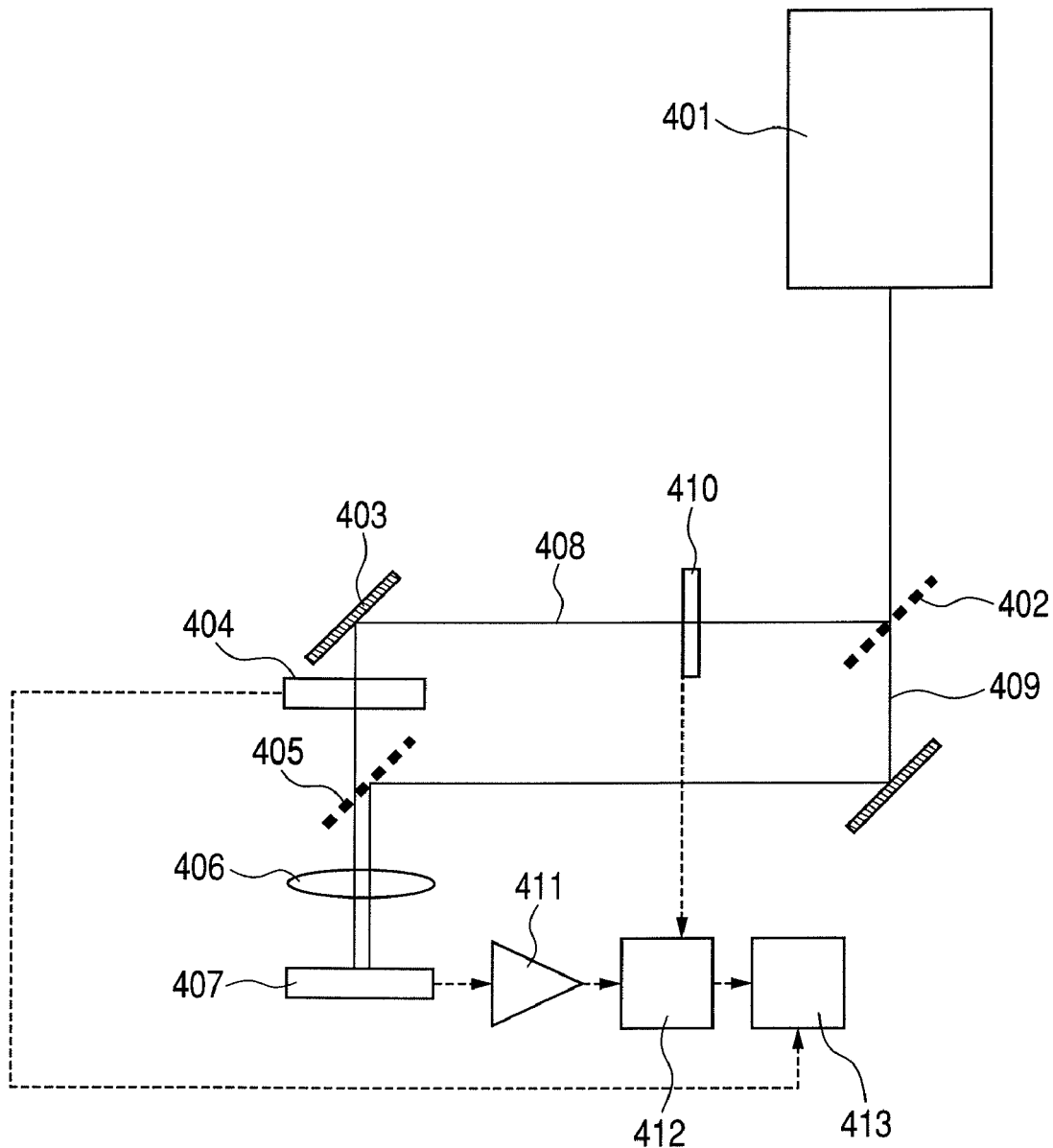
FIG. 4 is a drawing including a drive system for describing a second example using an acoustooptic device.

A second example will be described below. Although an inclination of the pumping light side mirror 203 is changed using the actuator 204 and the position 107 irradiated with the pumping light is moved along the first electrode 109 in the above-mentioned first example, an acoustooptic device 404 is used in this example (refer to FIG. 4). For example, by using an acoustooptic medium, such as chalcogenide glass, and driving this by a 10-MHz ultrasonic wave, beam deflection of approximately tens of milli-rad (1° to 2°) of an electromagnetic wave which is incident into the acoustooptic medium and passes this is obtained. Here, an electric signal for control is applied to an ultrasound generating unit, an ultrasonic wave is generated, this is put into the acoustooptic medium and beam deflection is performed. At this time, a deflection angle is changed by controlling the electric signal for control and changing a driving frequency of the ultrasonic wave, and a position irradiated with the pumping light is moved along the first electrode 109.

In this example, the position 107 irradiated with the pumping light is determined by a frequency of the ultrasonic wave which drives the acoustooptic device 404. Therefore, the above-mentioned time waveform is acquired by inputting information on the frequency of the above-mentioned ultrasonic wave, that is, an operating frequency of the acoustooptic device, into a computer 413 which is the processing unit.

In this example, by using the acoustooptic device, there are advantages that higher-speed drive can be performed, and that silence can be kept in an audible sound region even if high-speed drive is performed.

Third Example

To Install Irradiation Position in Reflecting Unit

Figure 5:
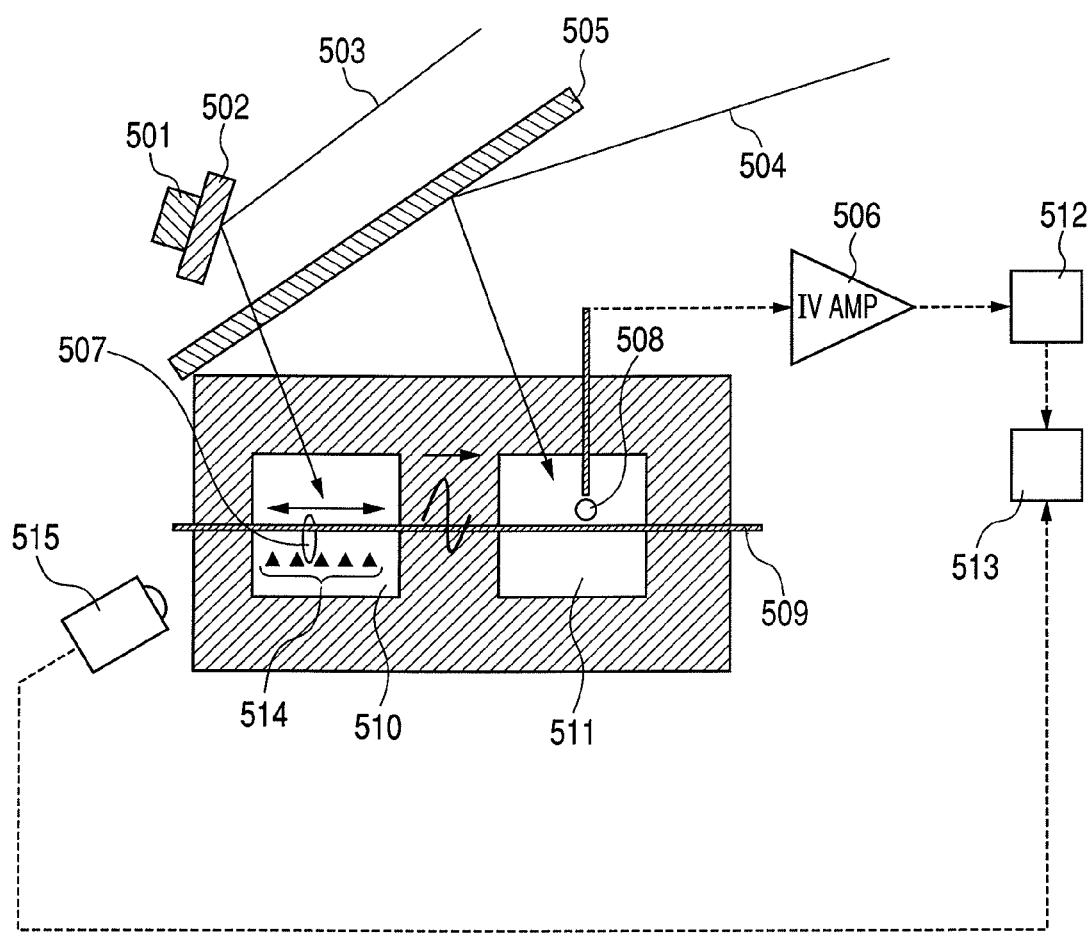
FIG. 5 is a drawing for describing a third example using an inspection element providing high reflectance markers.

A third example will be described below. In the above-mentioned first example, positional information on the position 107 irradiated with the pumping light is obtained by fetching a signal from the actuator 101 into the computer 120. In this example, in order to obtain more correctly a position irradiated with the pumping light, as illustrated in FIG. 5, a plurality of high reflectance markers 514 are installed near this along the first electrode 509. Similarly to the first electrode 509, the high reflectance markers 514 can be produced by stacking titanium and gold by the lift-off process by the photolithography and vacuum deposition method. It can be performed not to affect a terahertz wave which propagates in a microstrip line which uses a first electrode 509 as a signal line, by forming the high reflectance markers 514 separately to some extent from the first electrode 509.

Specifically, the plurality of them are installed in a position, which is separate by a distance which is approximately three times of its width from an edge of the first electrode 509, in equal intervals along the first electrode 509. Although their form is triangular in the illustrated example, it can take various forms, such as a line, according to cases.

As mentioned above, the inspection element of this example includes the following configuration. That is, it has a generating unit for generating an electromagnetic wave, a detecting unit for detecting the electromagnetic wave, and a propagating unit for propagating an electromagnetic wave generated in the generating unit to the detecting unit, and acquires information on a sample put on the propagating unit from a change of a propagating state of the electromagnetic wave. At least one side of the above-mentioned generating unit and the above-mentioned detecting unit has a photoconducting unit for generating or detecting an electromagnetic wave, and the photoconducting unit is configured to include two or more electrodes, including the first electrode and a second electrode, and a semiconductor film which has photoconductivity. The two or more electrodes of the photoconducting unit which includes the above-mentioned first electrode and the above-mentioned second electrode do not contact mutually, and are formed in contact with the above-mentioned semiconductor film, and the propagating unit is configured to include the above-mentioned first electrode, the above-mentioned second electrode, and a dielectric. A laser beam is irradiated in an electromagnetic wave generating position or an electromagnetic wave detecting position on the above-mentioned photoconduction film, and generation or detection of an electromagnetic wave is performed. Then, the above-mentioned one or more reflecting units (high reflectance markers) whose reflectances to the laser beam are different from that of the above-mentioned semiconductor film are provided along any of the above-mentioned two or more electrodes on the semiconductor film.

In this example, it is good to condense the pumping light 503 into a slender ellipse form, as illustrated. The pumping light 503 is condensed so that it may have a center near the first electrode 509 and its part may lap with the high reflectance markers 514. Thereby, when the position 507 irradiated with the pumping light moves along the first electrode 509, the pumping light is reflected (or dispersed) periodically whenever it is incident into the high reflectance markers 514. A photodetector 515 closely installed detects the pumping light reflected by the high reflectance markers 514. A computer 513 can obtain positional information on the position 507 irradiated with the pumping light by inputting a signal of the photodetector 515 into the computer 513.

Figure 6A:
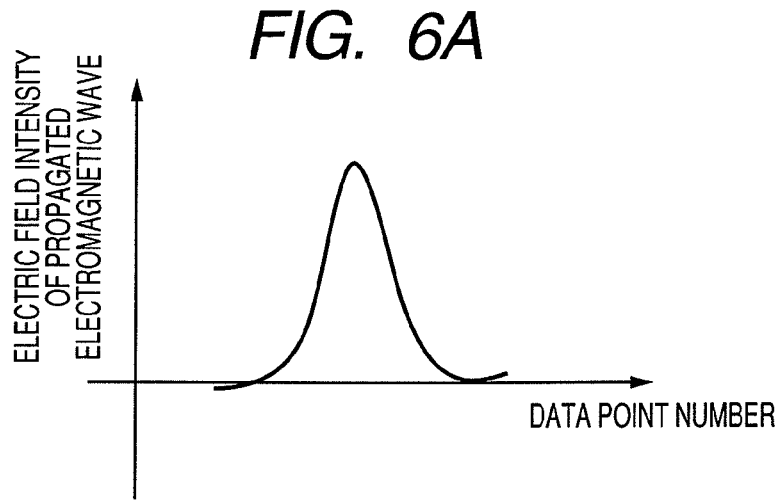
FIGS. 6A, 6B and 6C are drawings for describing a time waveform acquisition principle in the third example.
Figure 6B:
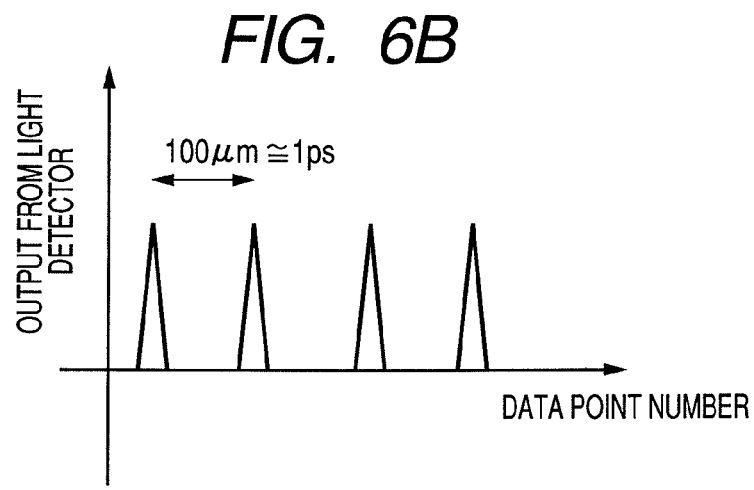
Figure 6C:
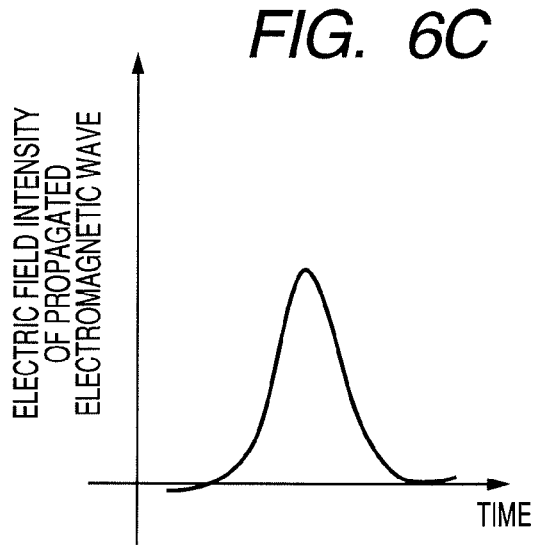

FIGS. 6A to 6C are schematic diagrams of signals acquired. In FIG. 6A, a horizontal axis is the data point number and a vertical axis is the electric field strength of a propagating electromagnetic wave. In FIG. 6B, a horizontal axis is the data point number and a vertical axis is the output from the photodetector 515. When pumping light laps with the high reflectance markers 514, a pulse-like signal is acquired. For example, when the high reflectance markers 514 are arranged in equal intervals in 100-μm gaps, it turns out that the pumping light 503 moved by 100 μm with adjacent pulse-like signals. When coordinate transformation is performed from the above-mentioned formula 1 using this result, a time waveform of the propagating electromagnetic wave as illustrated in FIG. 6C can be acquired.

In this example, a time waveform, delay time, and the like of a terahertz wave which propagates to the detecting unit can be found more accurately.

Fourth Example

Band Pass Filter

A fourth example will be described below. Although only the position irradiated with the pumping light is moved along the first electrode in the above-mentioned first example, both the pumping light 703 and the probe light 704 are moved along the first electrodes 708a and 708b, respectively in this example.

In this example, a band pass filter 701 produced with a metallic plane pattern is installed on the first dielectric 711. What titanium and gold are stacked is used for the above-mentioned metal plane pattern. Although the band pass filter 701 includes metal wires with specific length and width and an electromagnetic wave in a specific frequency is propagated, electromagnetic waves in the other frequencies are attenuated.

The first electrodes 708a and 708b are connected to the right and left of the band pass filter 701. The first electrode (left side) 708a and the first electrode (right side) 708b are insulated with the band pass filter 701 in direct current. Hence, a current-voltage conversion amplifier 705 is connected directly to the first electrode (right side) 708b for a time waveform to be able to be acquired.

In the above-mentioned configuration, an approximately 10V of voltage is applied to the first electrode (left side) 708a, and the pumping light 703 is irradiated near the first electrode 708a and on the first photoconductive film 709. In addition, in a similar manner, the first electrode (right side) 708b is connected to the amplifier 705, and the probe light 704 is irradiated near the first electrode (right side) 708b and on the second photoconductive film 710. When all of the pumping light 703 and the probe light 704 can be deflected with an actuator and the like, a position 706 irradiated with the pumping light and a position 707 irradiated with the probe light are movable along the first electrode (left side) 708a and first electrode (right side) 708b, respectively.

It is the same as the first example that delay time of a propagating electromagnetic wave can be shifted back and forth by moving the position 706 irradiated with the pumping light. In addition to it, probe light radiation time in FIGS. 3A to 3D can be shifted back and forth by moving the position 707 irradiated with the probe light.

Figure 7:
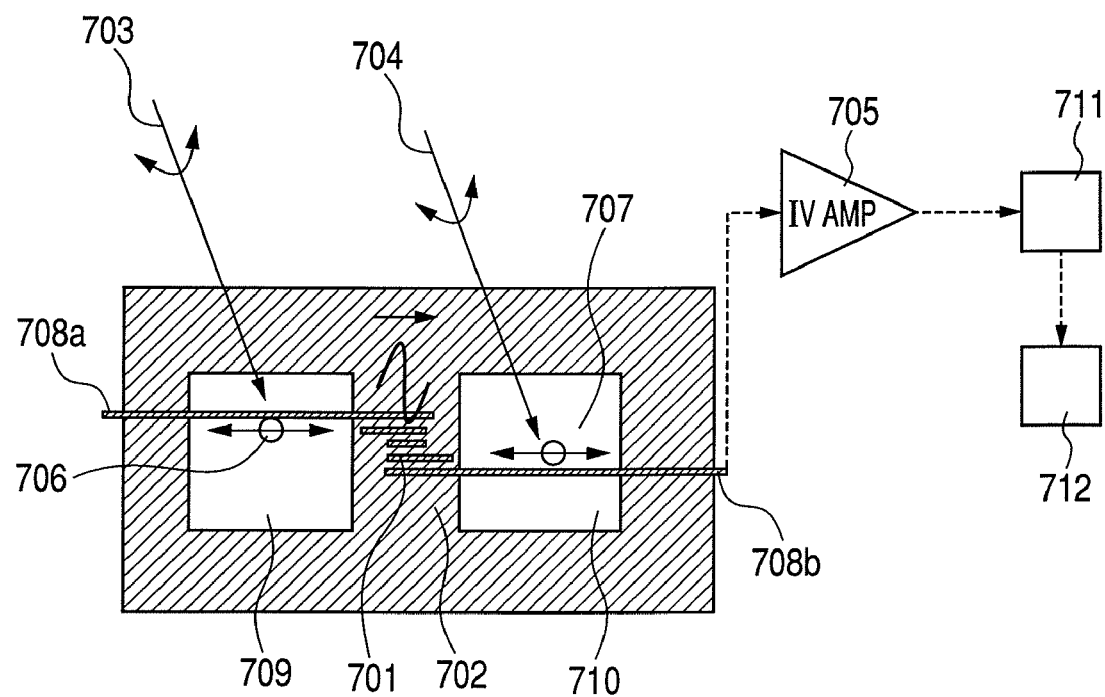
FIG. 7 is a drawing for describing a fourth example using a band pass filter.
Figure 8:
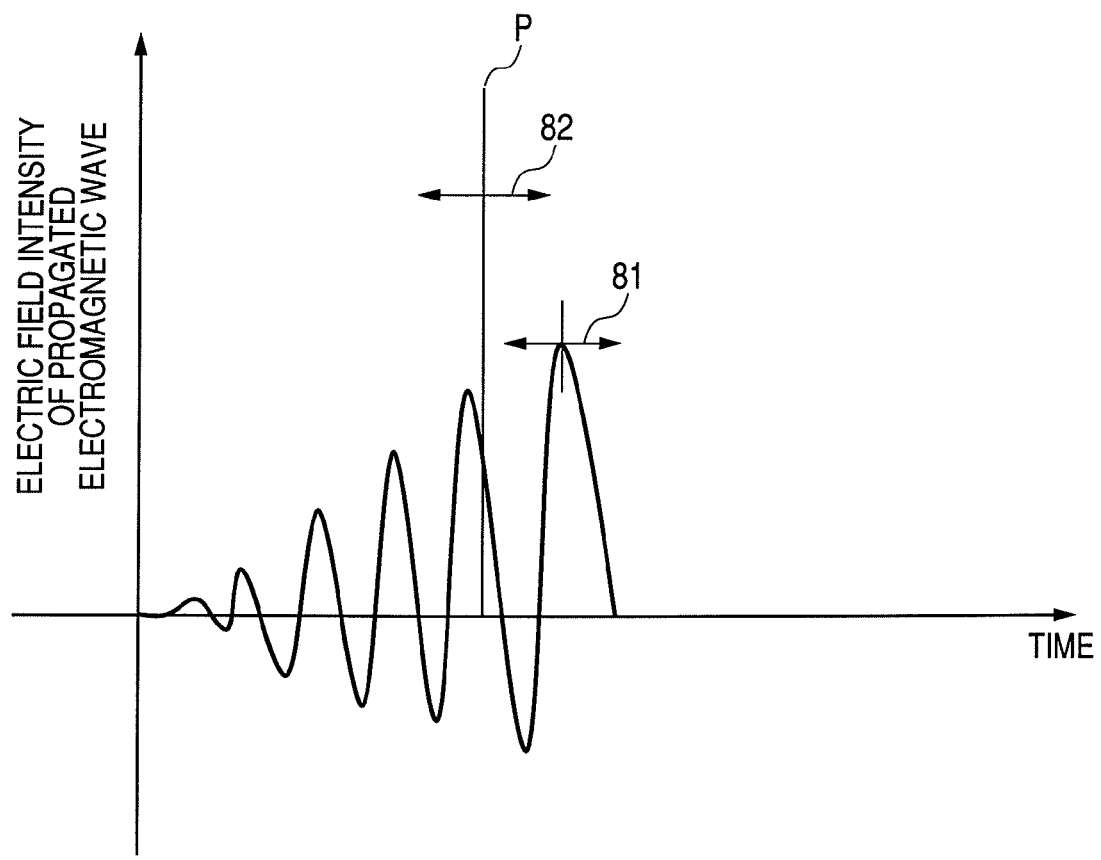
FIG. 8 is a drawing for describing a generation principle of time delay in the fourth example.

A schematic diagram is illustrated in FIG. 8. A horizontal axis is the time and a vertical axis is the electric field strength of a propagating electromagnetic wave. It becomes an oscillatory wave form by inserting the band pass filter 701. When the position 706 irradiated with the pumping light is shifted back and forth, as illustrated by an arrow 81, the time when a terahertz wave arrives at the position 707 irradiated with the probe light changes to the probe light radiation time P. On the other hand, when shifting back and forth the position 707 irradiated with the probe light, as illustrated in an arrow 82, the observation time (timing) shifts back and forth. Time delay occurs by changing a distance between the position 706 irradiated with the pumping light and the position 707 irradiated with the probe light, and a time waveform can be acquired. In FIG. 7, in particular, by moving the position 706 irradiated with the pumping light to a right end from a left end of the first photoconduction unit 709, and moving the position 707 irradiated with the probe light to a left end from a right end of the second photoconduction unit 710 simultaneously, a terahertz wave waveform is acquirable in a larger time domain. Specifically, in comparison with the case that only the position irradiated with the pumping light as illustrated in the first example is shifted back and forth, a time waveform of a terahertz wave propagating to the detecting unit can be acquired in a double time domain. Therefore, it is suitable when inspecting a sample with a large refractive index which gives a large change to a time waveform of a propagating terahertz wave. In addition, when a time waveform of a terahertz wave in a limited time domain is acquired, acquisition of a signal can be completed at double speed in comparison with the first example.

Fifth Example

Coplanar Strip Line

A fifth example will be described below. Although the generated electromagnetic wave propagates in the microstrip line type transmission line which includes the first electrode, first dielectric, and reference electrode in the above-mentioned first example, a so-called coplanar strip line is used in this example.

Figure 9A:
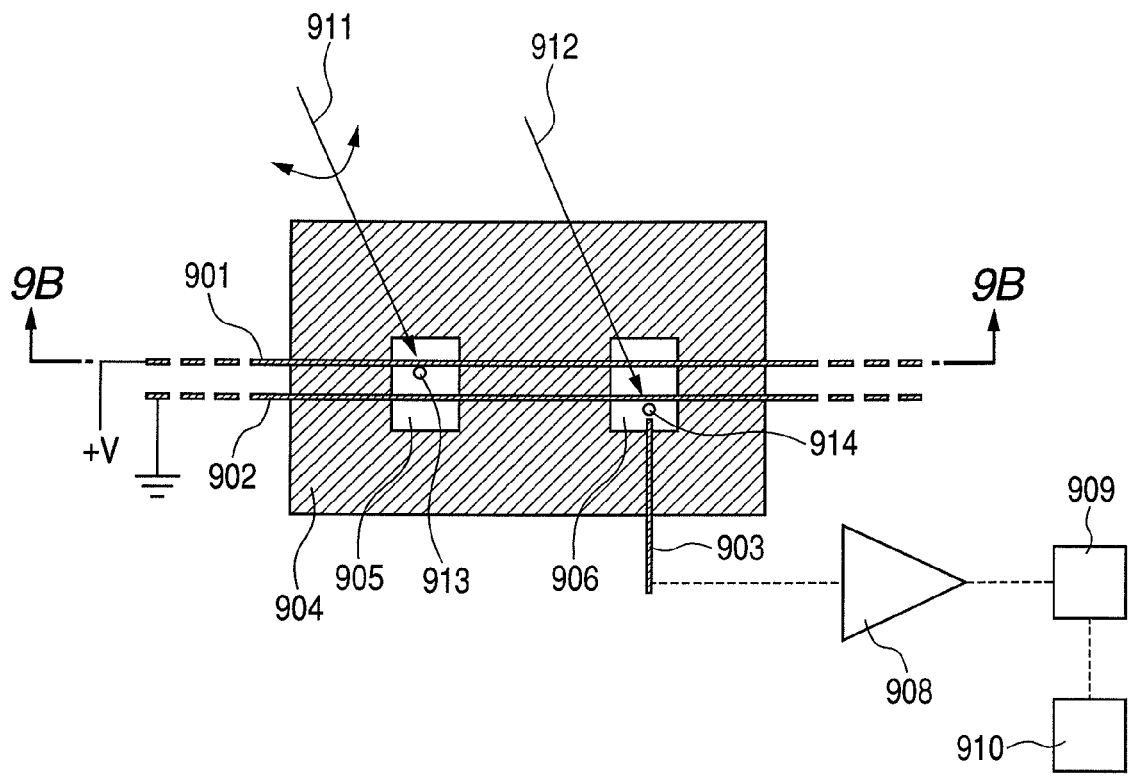
FIGS. 9A and 9B are drawings for describing a fifth example using a coplanar strip track type inspection element.
Figure 9B:
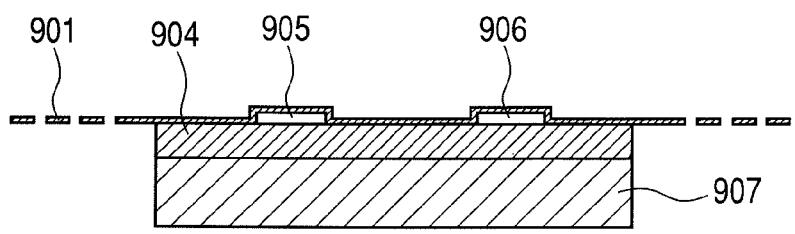

Schematic diagrams of this example are illustrated in FIGS. 9A and 9B. FIG. 9B illustrates a 9B-9B section in FIG. 9A. A layer of a dielectric 904, such as BCB, is formed on a substrates 907, such as Si, and a first photoconductive film 905 and a second photoconductive film 906 are installed on it. A thickness of the dielectric 904 is approximately 5 μm. LT-GaAs films installed by the epitaxial lift-off method or the like are used for the first and second photoconductive films 905 and 906. As for the photoconductive film and BCB, there are a method of bonding them by van der Waals bonding, and a method of bonding them using an epoxy resin or the like, but either is sufficient. Thereon, a first electrode 901, a second electrode 902, and a third electrode 903 which are made of stacking titanium and gold using the lift-off method are produced.

A voltage of approximately 10 V is applied to the first electrode 901, the second electrode 902 is grounded, and the third electrode 903 is connected to an amplifier 908. The second electrode 902 is equivalent to the reference electrode in the first example. By the same method as that in the first example, a laser beam from a mode locked titanium sapphire laser light source is divided into pumping light 911 and probe light 912. The pumping light 911 is irradiated near the first electrode 901 on the first photoconductive film 905. The probe light 912 is convergently irradiated in a clearance between the second electrode 902 and third electrode 903 on the second photoconductive film 906. As for the pumping light 911, the position 913 irradiated with the pumping light can be changed along the first electrode 901 by changing an angle of a mirror (not illustrated) with an actuator (not illustrated).

Also in this example, a position of irradiating pumping light is a position in which charge carriers generated in the semiconductor film by irradiation of the pumping light can conduct between two or more electrodes. This position is near the first electrode 901 or second electrode 902. More specifically, it is a near distance to such extent that the charge carriers generated by the irradiation of the laser beam conduct for a current to be generated by a potential difference generated between the first electrode and second electrode. The potential difference generated between the first electrode and second electrode includes also a potential difference induced by a propagating electromagnetic waves besides a potential difference generated by applying a voltage from the external.

The terahertz wave generated by pumping light radiation propagates in the coplanar strip track including the first electrode 901, second electrode 902, and dielectric 904, and arrives at the second photoconductive film 906 of the detecting unit. At the same time as a terahertz wave arrives at the second photoconductive film 906, the probe light 912 is irradiated in the position 914 irradiated with the probe light in the clearance (approximately 5 μm) between the second electrode 902 and third electrode 903.

Photo carriers generated in the second photoconductive film 906 by the irradiation of the probe light 912 are accelerated by the arriving terahertz wave, and a current is generated. The generated current is amplified by the amplifier 908, is detected by a lock-in amplifier 909, and is recorded by a computer 910.

A time waveform of a terahertz wave is acquired by moving the position 913 irradiated with the pumping light along the first electrode 901. In this example, there is such an advantage that production may become easy by making structure of a transmission line, which is a propagating unit, a coplanar strip track type. Also in this example, an acoustooptic device or the like may be used for movement of the position 913 irradiated with the pumping light, and in order to obtain the position irradiated with the pumping light accurately, a high reflectance marker or the like may be installed. Other respects are the same as those in the first example.

Sixth Example

To Open or Close Shutter Provided in Optical Path

A sixth example will be described below. Although a time waveform of a terahertz wave propagating into the detecting unit is acquired by moving pumping light along the first electrode in the above-mentioned first example, pumping light is made two or more to be irradiated in different positions respectively, and a shutter installed in an optical path of each pumping light is opened and closed in this example. In this way, the position irradiated with the pumping light is moved by switching the pumping light by the shutters.

That is, in this example, the above-mentioned distance changing unit switches the laser beam branched into two or more by opening/closing of a shutter, irradiates the above-mentioned electromagnetic wave generating position or the above-mentioned electromagnetic wave detecting position with it, and changes the electromagnetic wave generating position or the electromagnetic wave detecting position. Then, the above-mentioned processing unit receives information on switching of the above-mentioned laser beam to obtain change information of the propagating distance.

Figure 10:
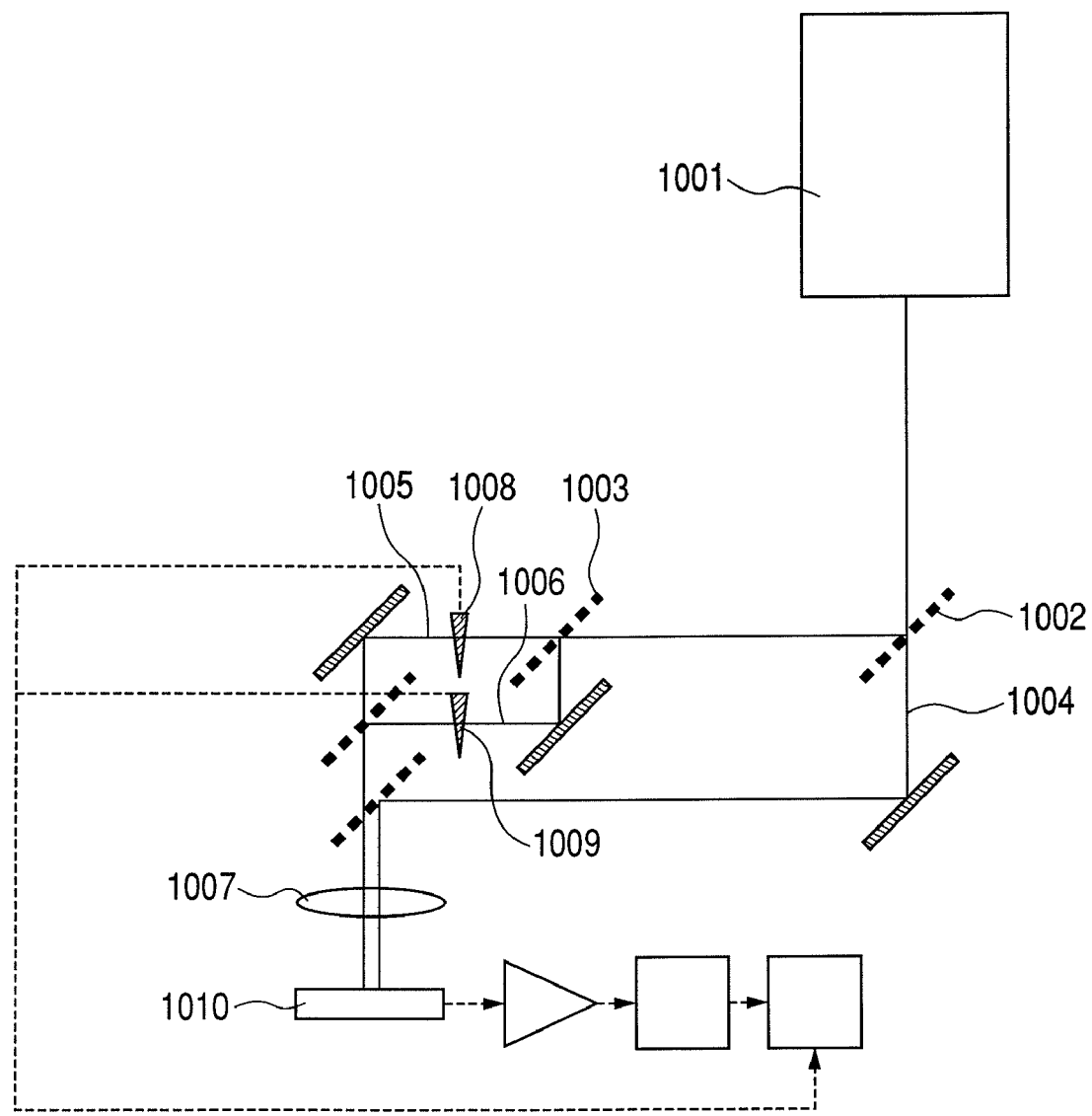
FIG. 10 is a drawing including a drive system for describing a sixth example using a shutter.
Figure 11:
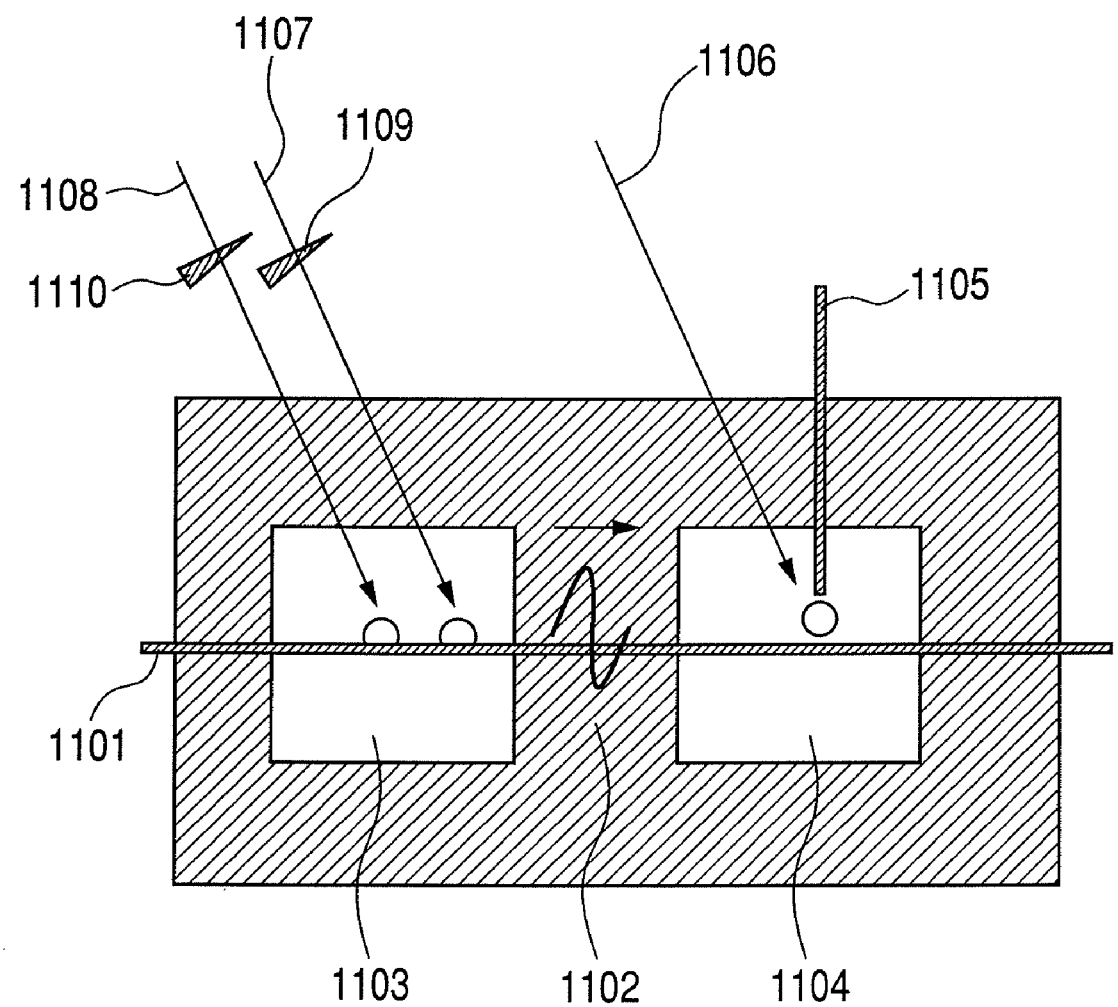
FIG. 11 is a drawing of an inspection element for describing the sixth example.

Description will be performed using FIGS. 10 and 11. The laser beam which emitted from a laser light source 1001 is divided into probe light 1004, first pumping light 1005, and second pumping light 1006 by a first beam splitter 1002 and a second beam splitter 1003. The first pumping light 1005 and second pumping light 1006 pass along the first shutter 1008 and second shutter 1009 respectively, and are incident into a device 1010 which is an inspection element through a lens 1007.

An enlarged view of the device 1010 in FIG. 10 is illustrated in FIG. 11. The probe light 1106 is convergently irradiated in a clearance between the first electrode 1101 and second electrode 1105 on the second photoconductive film 1104. The first pumping light 1107 and second pumping light 1108 are convergently irradiated in two different locations near the first electrode 1101 on the first photoconductive film 1103 through the first shutter 1109 and second shutter 1110, respectively. Here, the first shutter 1008 illustrated in FIG. 10 and the first shutter 1109 illustrated in FIG. 11 are the same products, and similarly, the second shutter 1009 illustrated in FIG. 10 and the second shutter 1110 illustrated in FIG. 11 also are the same products. In addition, similarly, the probe light 1004, first pumping light 1005, and second pumping light 1006 in FIG. 10 illustrate the same products as the probe light 1106, first pumping light 1107, and second pumping light 1108 in FIG. 11, respectively.

Figure 12A:
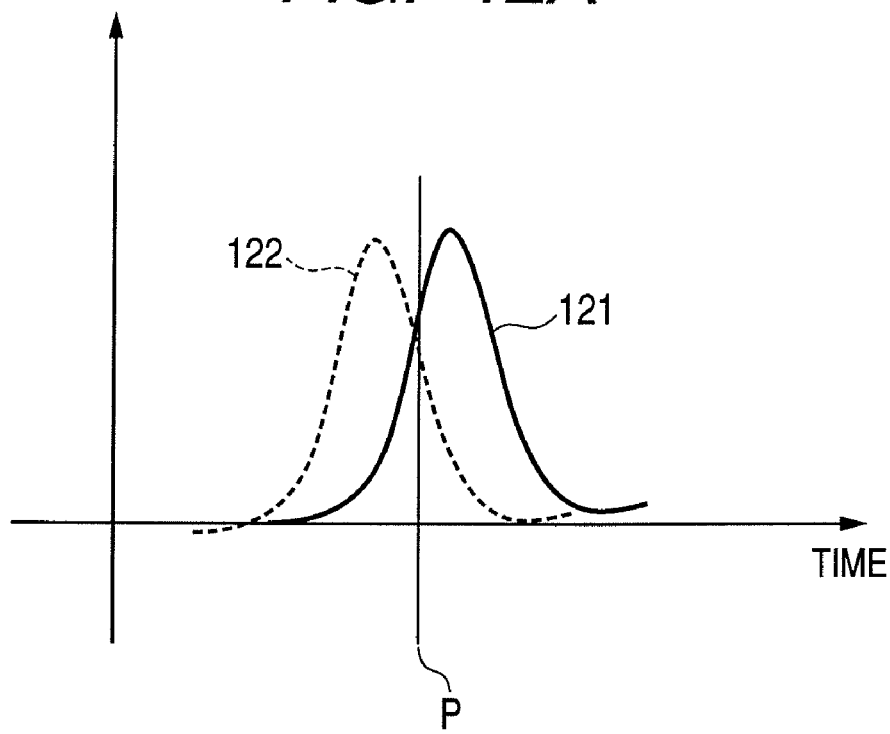
FIGS. 12A and 12B are drawings for describing a generation principle of time delay in the sixth example.

When the first 1109 shutter is opened and second shutter 1110 is closed, a terahertz wave generated by the first pumping light 1107 can be detected by irradiating the probe light 1106. At this time, a continuous line 121 in FIG. 12A illustrates a relation between the terahertz wave generated by the first pumping light 1107, and the probe light 1106 on the time axis. A value in front of a peak of the time waveform of the terahertz wave, which is generated in the generating unit and propagates into the detecting unit, is detectable by suitably setting an optical path length of the first pumping light 1107 and the probe light 1106. In addition, a straight line P on a time-axis in FIG. 12A illustrates the probe light irradiation time.

On the other hand, when the second shutter 1110 is opened and first shutter 1109 is closed, a terahertz wave generated by the second pumping light 1108 can be detected by irradiating the probe light 1106. At this time, a dotted line 122 in FIG. 12A illustrates a relation between the terahertz wave generated by the second pumping light 1108, and the probe light 1106 on the time axis. A value behind the peak of the time waveform of the terahertz wave, which propagates into the detecting unit, is detectable by suitably setting an optical path length of the second pumping light 1108 and the probe light 1106. Such difference of detection is derived from time delay generated since an irradiation position of the second pumping light 1108 is further distant from the irradiation position of the probe light 1106 in comparison with the first pumping light 1107.

Figure 12B:
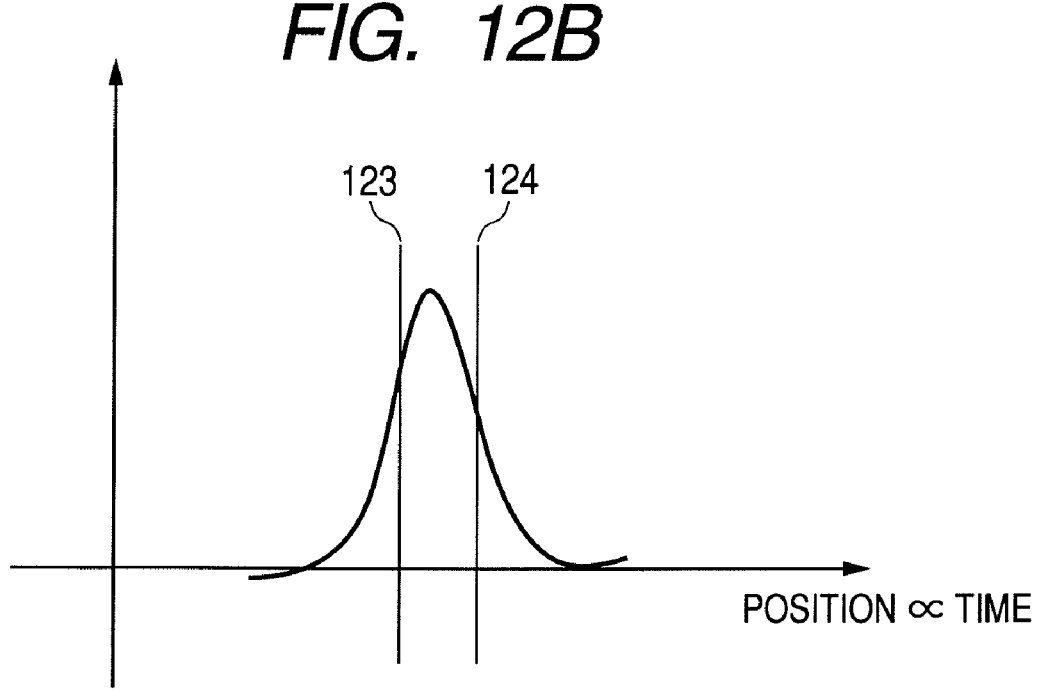

About the above mentioned, when coordinate transformation of space and time of the above-mentioned formula 1 is performed similarly to the first example, it becomes as illustrated in FIG. 12B. That is, each of a point relating to the first pumping light 1107 and a point relating to the second pumping light 1108 corresponds to each of both sides 123 and 124 sandwiching the peak of the time waveform of the terahertz wave propagating into the detecting unit.

When the first shutter 1109 and second shutter 1110 are opened and closed by turns and each differential value of values then acquired in the detecting unit is obtained, an approximate peak position of the time waveform of the terahertz wave propagating into the detecting unit can be known. For example, when the differential value is close to zero, it turns out that a peak exists near the middle of the point relating to the first pumping light 1107, and the point relating to the second pumping light 1108. Here, when time delay occurs in a propagating terahertz wave by dropping or installing a sample on the first electrode 1101 on the first dielectric 1102 similarly to the first example, a peak position shifts toward the first position irradiated with the pumping light in FIG. 12B. Therefore, a differential value takes a value except zero and it can be detected that the sample is dropped. In addition, it can be also performed from magnitude of the differential value to guess a type of the sample.

In this example, when opening and closing the first shutter 1109 and second shutter 1110 by turns, measurement of only two points on the time-axis can be performed at high speed. Of course, the number of pumping light and shutters can be also increased from 2. In this case, it can be performed by sequentially opening and closing the shutter so as to irradiate respective pumping light near the first electrode 1101 on the first photoconductive film 1103 with enlarging a distance gradually along an electrode stretching direction to measure the time waveform of the propagating terahertz wave more accurately.

Seventh Example

To Propagate in Photoconductive Film

Figure 13A:
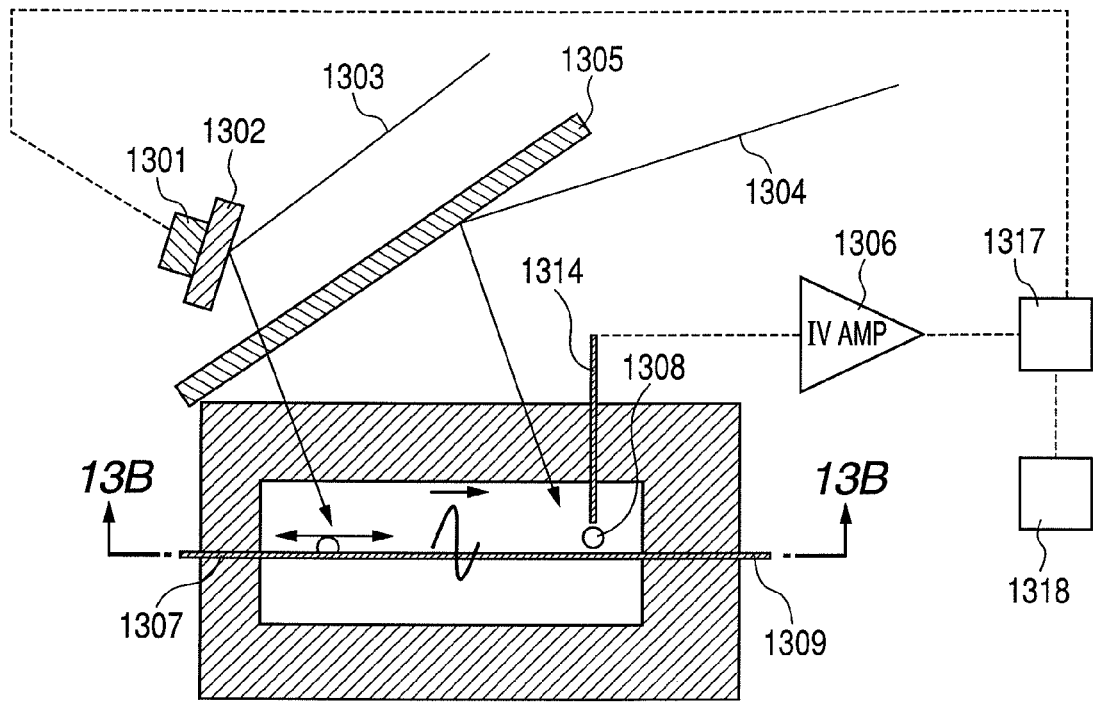
FIGS. 13A, 13B and 13C are drawings for describing a seventh example.
Figure 13B:
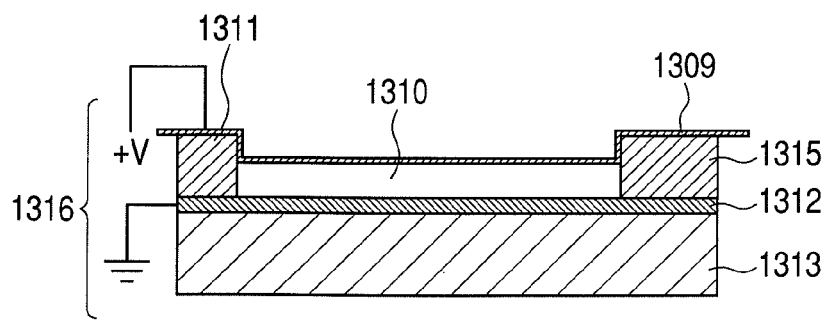

A seventh example of the present invention will be described using FIGS. 13A to 13C. FIG. 13B illustrates a 13B-13B section in FIG. 13A. As illustrated in FIGS. 13A and 13B, in this example, an LT-GaAs film serves as a first dielectric part in the first example by installing one sheet of wide LT-GaAs film. That is, the seventh example has structure of replacing the first photoconductive film 110, first dielectric 111, and second photoconductive film 112 in the first example with the first photoconductive film 1310. The terahertz wave generated in the position 1307 irradiated with the pumping light on the first photoconductive film 1310 propagates in a microstrip line, which includes a first electrode 1309 and a reference electrode 1312, with using the first photoconductive film 1310 as the dielectric. Then, it is detected by the position 1308 irradiated with the probe light on the first photoconductive film 1310. Such a configuration has an advantage of reducing reflected pulses accompanying impedance mismatching of the microstrip line. Other respects are the same as those in the first example.

Figure 13C:
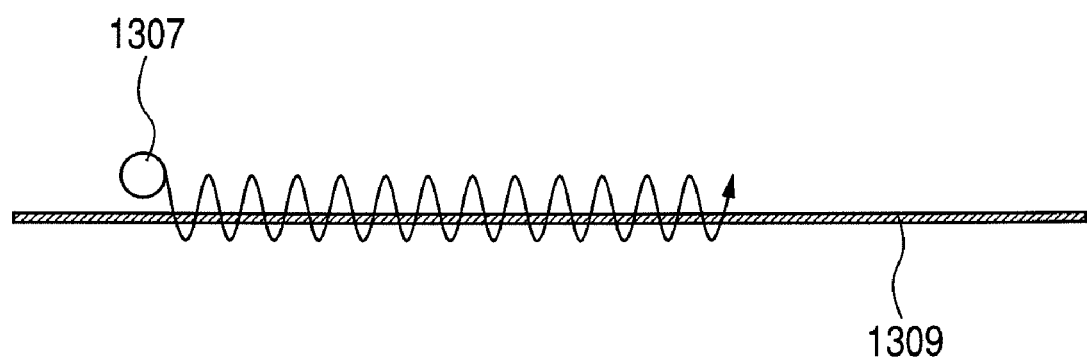

In addition, in this example, it can be performed not only to move the position 1307 irradiated with the pumping light along the first electrode 1309 as illustrated in FIG. 13C, but also to make it scan wavelike so as to straddle the first electrode 1309. This is performed using an actuator 1301. The terahertz wave to be generated is modulated because the position 1307 irradiated with the pumping light straddles the first electrode 1309. With synchronizing with this modulation, synchronous detection is performed by the lock-in amplifier 1317. For this reason, an operation situation of the actuator 1301 is input into the lock-in amplifier 1317 as a reference signal of the modulation. That is, here, the position of irradiating a laser beam is changed, an electromagnetic wave which is generated in the above-mentioned electromagnetic wave generating position is modulated, and the synchronous detection of the modulated electromagnetic wave is performed. By executing such a method, further high-speed time waveform acquisition is achievable.

Eighth Example

Variable Angle Mirror and Moving Parabolic Mirror

An eighth example of the present invention will be described using FIGS. 14AA to 14AD. A photoconductive antenna array element 1501 illustrated in FIGS. 14AA to 14AD is an element which generates a terahertz wave. On an LT-GaAs thin film which is given crystal growth on a gallium arsenide substrate, multiple arraying of so-called dipole antenna type of electrodes is performed. A gap between two adjacent electrodes which configure a dipole antenna is typically 5 μm, and a space between adjacent antennas is approximately 500 μm. When approximately 10 V of voltage is applied between both electrodes, and pumping light 1502 (a femtosecond laser with a pulse time width of approximately 100 fs) is irradiated in an antenna gap, a pulse-like terahertz wave is generated.

The pumping light 1502 is incident into the photoconductive antenna array element 1501 by a variable angle mirror 1503. The pumping light 1502 is irradiated in a gap between electrodes of one arbitrary dipole antenna out of two or more arranged ones on the photoconductive antenna array element 1501.

A part of generated terahertz wave is emitted from a back side of the photoconductive antenna array element 1501, is collimated with a moving parabolic mirror 1504, and is sent to a fixed parabolic mirror 1505. The fixed parabolic mirror 1505 convergently irradiates a terahertz wave on the photoconduction antenna element 1506. As for the photoconduction antenna element 1506, although a dipole antenna is formed on LT-GaAs similarly, the number of the antenna is one. A pulse of a terahertz wave and a probe light (a femtosecond laser same as pumping light) pulse are simultaneously incident in the gap between electrodes which configures the antenna. The terahertz wave is detected by detecting a current generated at this time.

Here, supposing an angle of the variable angle mirror 1503 is changed and a position which the pumping light 1502 irradiates is moved from an edge of the photoconductive antenna array element 1501 to another edge. Supposing ten dipole antennas are arranged in a line at intervals of 500 μm at this time, it means that the terahertz wave generating position moves 5 mm. Supposing the photoconductive antenna array element 1501 and variable angle mirror 1503 are separate enough and it can be regarded that there is no change of an optical path length of the pumping light 1502 due to changing an angle of the variable angle mirror.

Figure 14A:
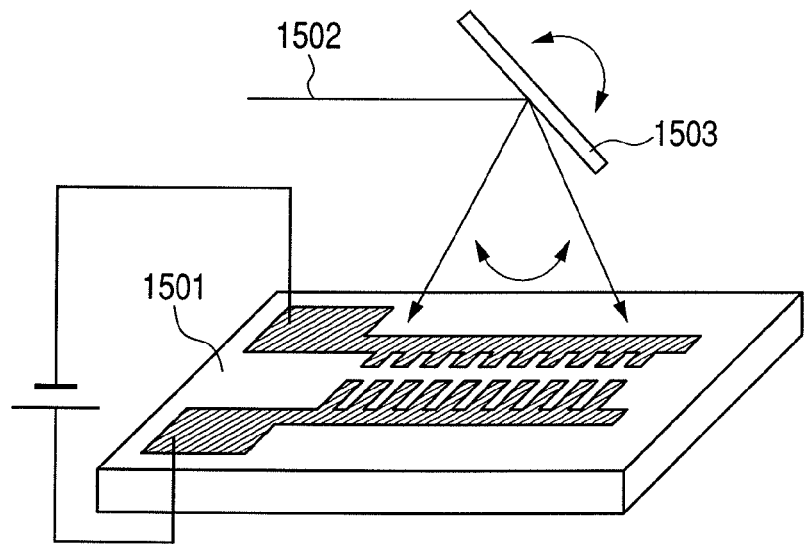
FIGS. 14AA, 14AB, 14AC, 14AD, 14BA, 14BB, 14BC and 14BD are drawings for describing movement of a position of irradiation of a pumping beam in eighth and ninth examples.
Figure 14A:
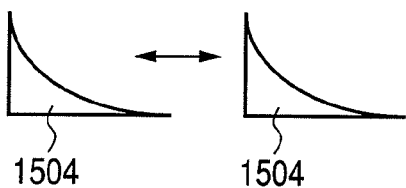
Figure 14A:
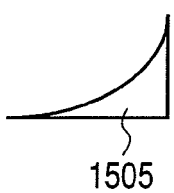
Figure 14A:
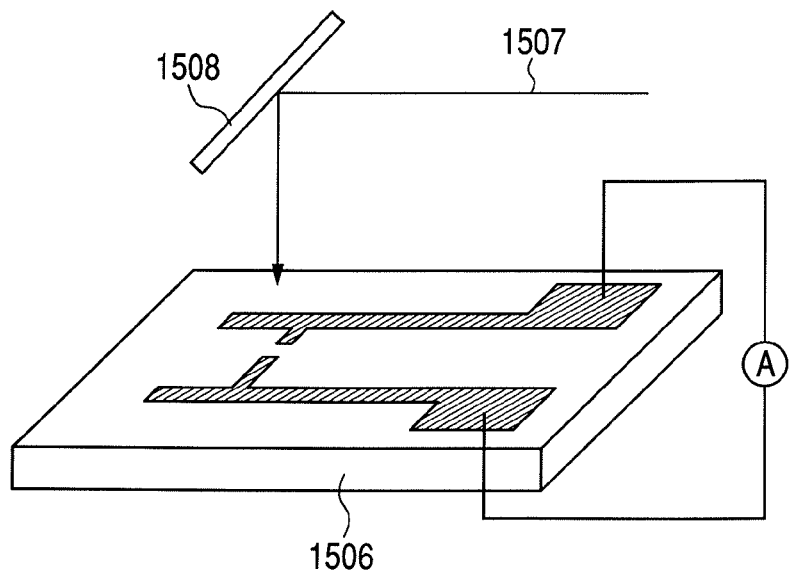

According to movement of a terahertz wave generating position, the moving parabolic mirror 1504 also is moved by 5 mm in directions in FIGS. 14AA to 14AD. Then, in the photoconduction antenna element 1506, a shift occurs in timing when the probe light 1507 and terahertz wave are incident, and the time waveform of the terahertz wave can be acquired by this.

When the terahertz wave generating position moves by 5 mm (a moving direction is a direction in which the moving parabolic mirror 1504 keeps away from the fixed parabolic mirror 1505) at intervals of 500 μm, a terahertz wave time waveform can be acquired in a duration of 16.7 ps at intervals of 1.67 ps.

By the method of the present invention, a time waveform of a terahertz wave emitted to a space is acquirable without a return optical system.

Ninth Example

Variable Angle Mirror and Fixed Parabolic Mirror

Figure 14B:
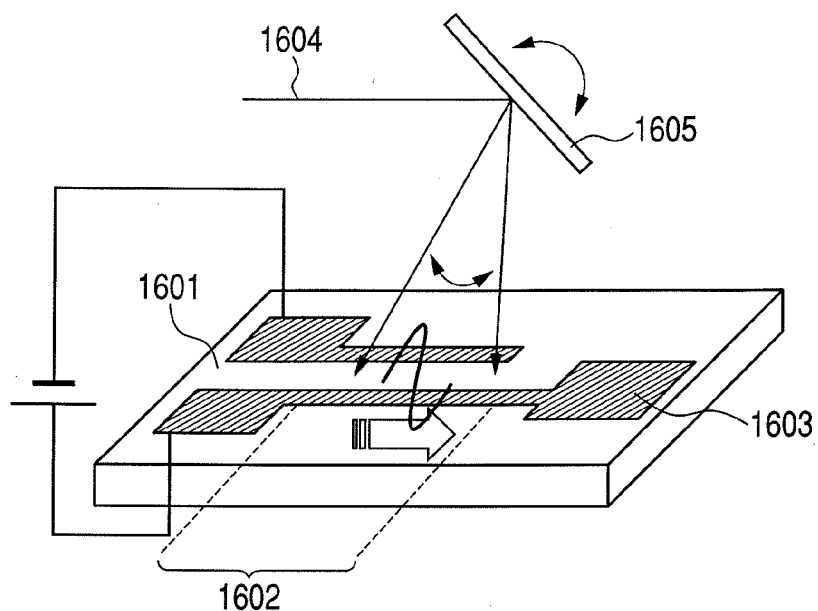
Figure 14B:
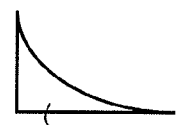
Figure 14B:
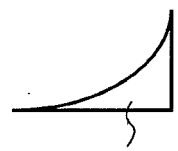
Figure 14B:
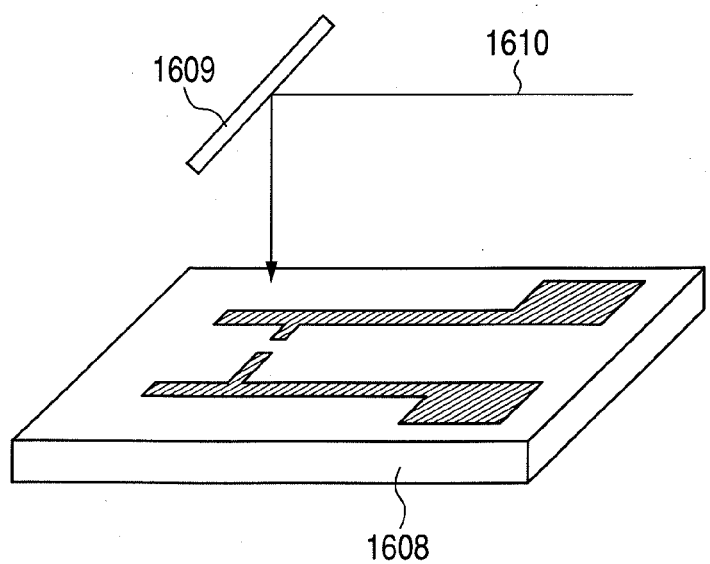

A ninth example of the present invention will be described using FIGS. 14BA to 14BD. As for a generation side photoconduction antenna element 1601 which generates a terahertz wave, a coplanar strip line 1602 and an antenna 1603 are formed on a LT-GaAs thin film. As for the coplanar strip line 1602, metal wires which have a width of approximately 20 μm are formed with having a gap of approximately 100 μm. One side of the coplanar strip line is connected to the antenna 1603.

Approximately 10 to 100 V of voltage is applied between both the metal wires of the coplanar strip line, and its clearance is irradiated with pumping light 1604. The pumping light 1604 can move an irradiation position along a direction, in which the coplanar strip line 1602 is extended, by the variable angle mirror 1605. The terahertz wave generated in the position irradiated with the pumping light propagates in the coplanar strip line 1602, and is emitted to the space with then antenna 1603. In addition, the antenna illustrated in the figure is schematic and does not illustrate an actual antenna shape.

The terahertz wave emitted in the space is detected by a detection side photoconduction antenna element 1608 through fixed parabolic mirrors 1606 and 1607.

Here, supposing the coplanar strip line 1602 has a length of 5 mm and an irradiation position of the pumping light 1604 can move by 5 mm along the coplanar strip line 1602. Then, when the terahertz wave generating position moves by 5 mm, a change arises in an optical path length. The time waveform of a terahertz wave can be acquired using this.

Supposing an effective refractive index in the coplanar strip line on LT-GaAs is approximately 3, it is equivalent to 15 mm in an optical path length. Therefore, in the range of approximately 50 ps in a time domain, a terahertz wave time waveform is acquirable.

In this example, since a terahertz wave generating position can be moved continuously, acquisition of a smooth time waveform is attainable.

Tenth Example

Movable Stage

Figure 15:
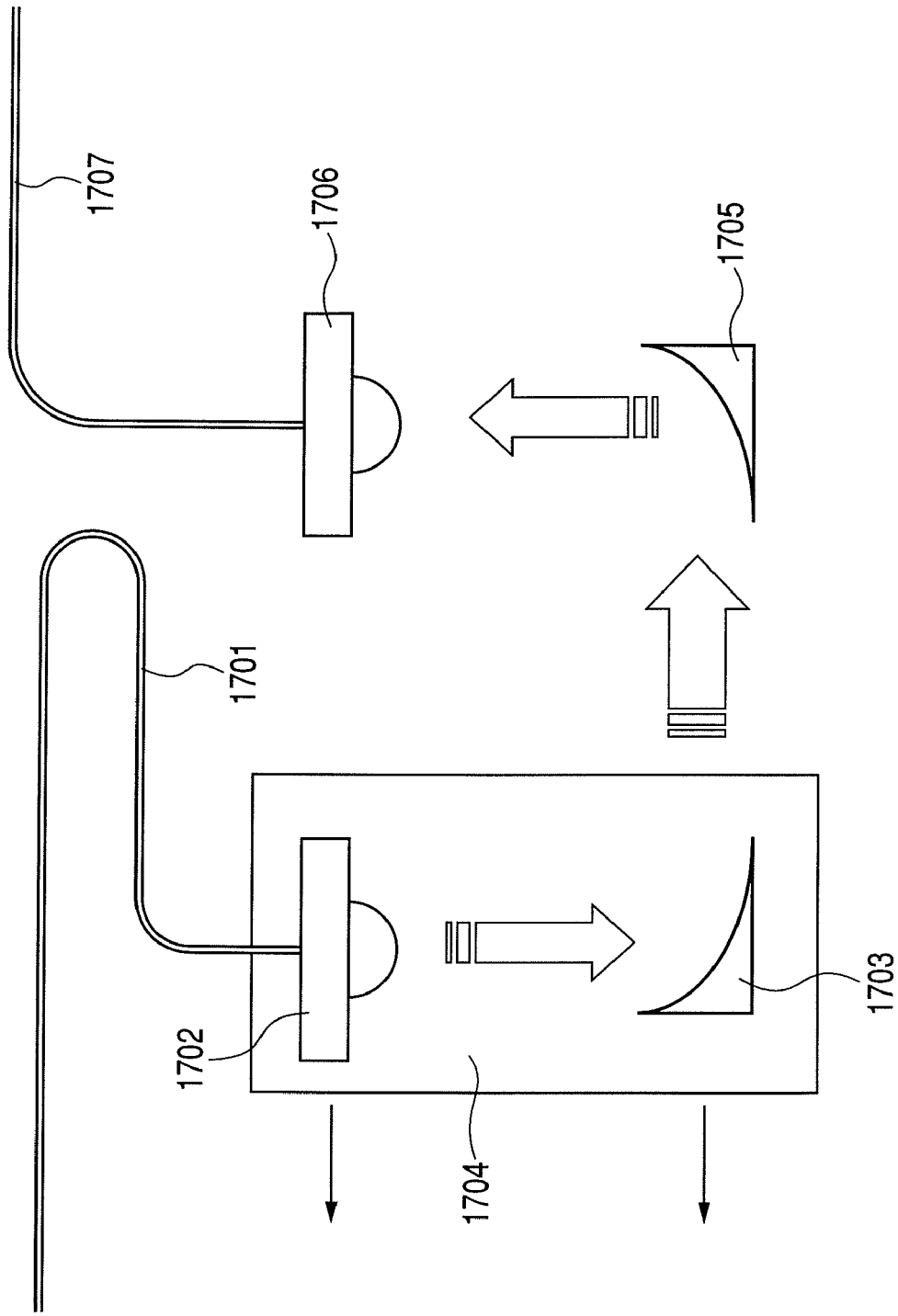
FIG. 15 is a drawing for describing movement of generating position of a terahertz wave in a tenth example.

A tenth example of the present invention will be described using FIG. 15. As for a generation side photoconduction antenna element 1702 which generates a terahertz wave, a dipole antenna (not illustrated) is formed on LT-GaAs. The pumping light to the generation side photoconduction antenna 1702 propagates in an optical fiber 1701, and is irradiated directly in a predetermined position of the above-mentioned dipole antenna. The terahertz wave generated from the generation side photoconduction antenna element 1702 is collimated with a parabolic mirror 1703, and is incident into a detection side photoconduction antenna element 1706 through a parabolic mirror 1705. At the same time as the terahertz wave is incident into the detection side photoconduction antenna element 1706, the probe light propagates in an optical fiber 1707 and is incident.

Here, the generation side photoconduction antenna element 1702 and parabolic mirror 1703 are held on a stage 1704 (movable stage). Since an optical path length of a terahertz wave changes when the stage 1704 (movable stage) is moved in a direction (left) shown by an arrow in the figure, timings when the terahertz wave and probe light are incident into the detection side photoconductive element 1706 change. The time waveform of the terahertz wave can be acquired using this.

For example, by moving the stage (movable stage) by 10 mm to the left, time for the terahertz wave to arrive at the detection side photoconductive element 1706 is delayed by approximately 33.3 ps. That is, the time waveform of the terahertz wave over 33.3 ps is acquirable in a time domain.

When the pumping light and probe light are made to be incident into each of the generation side and detection side photoconductive antenna elements using the optical fiber, so-called time and effort of optical adjustment is reduced greatly, and an apparatus strong against vibration and the like can be made. However, in a delay optical system using the Littrow reflector which is a conventional method, an optical fiber cannot be used in a Littrow reflector part. For this reason, a unit of taking out a laser beam once from an optical fiber, and making it be incident into the optical fiber again after passing through the delay optical system has been used. However, in the method of this example, since a Littrow reflector is not used, an optical fiber can be used in a full laser path.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2007-310462, filed Nov. 30, 2007, which is hereby incorporated by reference herein in its entirety.

The invention claimed is:

1. An apparatus for acquiring information on a time wave form of a terahertz wave, comprising:
 a generating unit for generating a terahertz wave;
 a detecting unit for detecting waveform information of a terahertz wave generated by the generating unit;
 a distance changing unit for changing a first position in the generating unit into a third position therein or a second position in the detecting unit into a fourth position to change a propagating distance of the terahertz wave from the first position to the second position; and
 a control unit for controlling the distance changing unit so that first waveform information of the terahertz wave generated at the first position is detected and subsequently, second waveform information of the terahertz wave generated at the third position is detected at the second position or second waveform information of the terahertz wave generated at the first position is detected at the fourth position,
 wherein information on the time waveform of the terahertz wave is acquired by using the first and second waveform information detected in the detecting unit.

2. The apparatus according to claim 1,
 wherein the apparatus comprises:
 a substrate having the generating unit and the detecting unit; and
 a propagating unit for making a terahertz wave generated at the first position propagate to the second position, the propagating unit being provided on the substrate and being in contact with the generating unit and the detecting unit, and
 wherein the distance changing unit changes a position to be irradiated with excitation light from the first position into the third position or from the second position into the fourth position.

3. The apparatus according to claim 2,
 wherein a plurality of reflection units having a reflectance different from a reflectance for the excitation light in the generating unit or the detection unit are provided along the propagating unit, and
 wherein the distance changing unit is a variable angle mirror.

4. The apparatus according to claim 1,
 wherein the apparatus has a moving parabolic mirror for making a terahertz wave generated in the generating unit propagate to the detecting unit through a space,
 wherein the distance changing unit is a variable angle mirror to change a position to be irradiated with excitation light from the first position into the third position or from the second position into the fourth position, and
 wherein the variable angle mirror and the moving parabolic mirror are integrated or operated as linked with each other.

5. An inspection apparatus for inspecting a sample by using information as to a time waveform of terahertz wave acquired by the apparatus according to claim 1, the sample being disposed between the generating unit and the detecting unit,
 wherein the generating unit and the detecting unit contain a photoconductive film and an electrode in contact with the photoconductive film, and
 wherein a ratio between a pulse frequency which determines timings of generating a pulse of a terahertz wave from the generating unit and a sampling frequency which determines timings of detecting waveform information of a terahertz wave in the detecting unit is n:1, where n is a natural number of one or more.

6. The inspection apparatus according to claim 5, wherein the distance changing unit changes the first position into the third position or changes the second position into the fourth position using an acoustooptic device through which a laser beam passes or a shutter capable of opening and closing branched laser beams.

7. The apparatus according to claim 1,
 wherein the terahertz wave generated in the generating unit propagates to the detecting unit through a space, and
 wherein the distance changing unit is a movable stage for changing a relative position between the generating unit and the detecting unit.

8. The apparatus according to claim 1, wherein the distance changing unit changes the first position to the third position and the control unit controls the distance changing unit so that the second waveform information of the terahertz wave generated at the third position is detected at the second position.

9. The apparatus according to claim 1, wherein the distance changing unit changes the second position to the fourth position and the control unit controls the distance changing unit so that the second waveform information of the terahertz wave generated at the first position is detected at the fourth position.

10. A method for acquiring information on a time waveform of a terahertz wave comprising the steps of:
 generating a terahertz wave at a first position in a generating unit;
 detecting first waveform information of the terahertz wave at a second position in a detecting unit;
 changing the first position into a third position in the generating unit or changing the second position into a fourth position in the detecting unit to change a propagating distance of the terahertz wave from the first position to the second position;
 detecting second waveform information of the generated terahertz wave after the change from the first position into the third position or from the second position into the fourth position; and
 acquiring information on a time waveform of the terahertz wave using the first and second waveform information.

11. A terahertz time domain spectroscopy method comprising the steps of generating a terahertz wave, propagating the generated terahertz wave, detecting information on the propagated terahertz wave, and configuring a time waveform of the terahertz wave from information on the detected terahertz wave, wherein a position generating or detecting the terahertz wave is changed in order to obtain the time waveform.

* * * * *